United States Patent [19]
Gardiner et al.

[11] Patent Number: 6,149,658
[45] Date of Patent: Nov. 21, 2000

[54] SUTURED STAPLE SURGICAL FASTENERS, INSTRUMENTS AND METHODS FOR MINIMALLY INVASIVE VASCULAR AND ENDOSCOPIC SURGERY

[75] Inventors: Barry N. Gardiner, Orinda; Paul T. McDonald, Oakland; Richard D. Phipps, Morgan Hill, all of Calif.

[73] Assignee: Coalescent Surgical, Inc., Sunnyvale, Calif.

[21] Appl. No.: 08/781,579

[22] Filed: Jan. 9, 1997

[51] Int. Cl.[7] ................................................. A61B 17/10
[52] U.S. Cl. ............................................. 606/139; 606/144
[58] Field of Search .................................... 606/139, 144, 606/151, 222, 219

[56] References Cited

U.S. PATENT DOCUMENTS

| | | | |
|---|---|---|---|
| 2,201,610 | 5/1940 | Dawson | 128/337 |
| 2,430,293 | 11/1947 | Howells | 1/47 |
| 3,082,426 | 3/1963 | Miles | 1/349 |
| 3,150,379 | 9/1964 | Brown | 1/349 |
| 4,111,206 | 9/1978 | Vishnevsky et al. | 128/305 |
| 4,129,059 | 12/1978 | Van Eck | 85/49 |
| 4,465,071 | 8/1984 | Samuels et al. | 128/335 |
| 4,470,533 | 9/1984 | Schuler | 227/19 |
| 4,532,927 | 8/1985 | Miksza, Jr. | 128/334 |
| 4,586,503 | 5/1986 | Kirsch et al. | 128/334 |
| 4,595,007 | 6/1986 | Mericle | 128/334 |
| 4,890,615 | 1/1990 | Caspari et al. | 606/146 |
| 4,923,461 | 5/1990 | Caspari et al. | 606/146 |
| 4,929,240 | 5/1990 | Kirsch et al. | 606/151 |
| 4,957,498 | 9/1990 | Caspari et al. | 606/146 |
| 5,032,127 | 7/1991 | Frazee et al. | 606/143 |
| 5,035,692 | 7/1991 | Lyon et al. | 606/143 |
| 5,222,961 | 6/1993 | Nakao et al. | 606/143 |
| 5,250,053 | 10/1993 | Snyder | 606/145 |
| 5,304,204 | 4/1994 | Bregen | 606/219 |
| 5,366,459 | 11/1994 | Yoon | 606/151 |
| 5,366,479 | 11/1994 | McGarry et al. | 606/219 |
| 5,431,666 | 7/1995 | Sauer et al. | . |
| 5,437,680 | 8/1995 | Yoon | 606/139 |
| 5,437,681 | 8/1995 | Meade et al. | 606/145 |
| 5,445,167 | 8/1995 | Yoon et al. | 128/898 |
| 5,496,334 | 3/1996 | Klundt et al. | 606/145 |
| 5,571,119 | 11/1996 | Atala | 606/146 |
| 5,603,718 | 2/1997 | Xu | 606/145 |
| 5,630,540 | 5/1997 | Blewett | 227/176.1 |
| 5,658,312 | 8/1997 | Green et al. | 606/219 |

FOREIGN PATENT DOCUMENTS

| | | | |
|---|---|---|---|
| 0 122 046 A1 | 10/1984 | European Pat. Off. | A61B 17/12 |
| 129441 | 12/1984 | European Pat. Off. | 17/8 |
| 0 072 232 A2 | 2/1992 | European Pat. Off. | A61B 17/12 |
| 0 598 529 | 5/1994 | European Pat. Off. | A61B 17/12 |
| 0 656 191 A2 | 6/1995 | European Pat. Off. | A61B 17/128 |
| 377052 | 6/1923 | Germany . | |
| 7-308322 | 11/1995 | Japan | A61B 17/10 |
| 8-336544 | 12/1996 | Japan | A61B 17/72 |
| WO 97/12555 | 4/1997 | WIPO | A61B 17/04 |

*Primary Examiner*—Michael Buiz
*Assistant Examiner*—Lien Ngo
*Attorney, Agent, or Firm*—Majestic, Parsons, Siebert & Hsue, P.C.

[57] ABSTRACT

A sutured staple, instrument and method are provided for constructing a graft-to-artery anastomosis and other soft tissue anastomoses, particularly by minimally invasive (or endoscopic) surgery. The sutured staple is comprised of a needle, pin, base and flange. The needle allows this surgical staple to be sewn through, for example, a graft and artery to be joined, and the pin, base and flange are formed to seal the graft and artery together between cooperating surfaces of the base and flange. The instrument holds the staple at its distal or working end, and controls in the handle allow application of the staple. The method employs the sutured staples and instrument to join soft tissues and to construct graft-to-artery anastomoses.

47 Claims, 19 Drawing Sheets

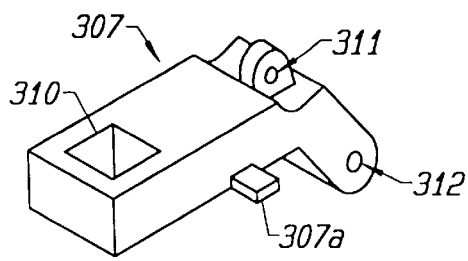
FIG. 3C
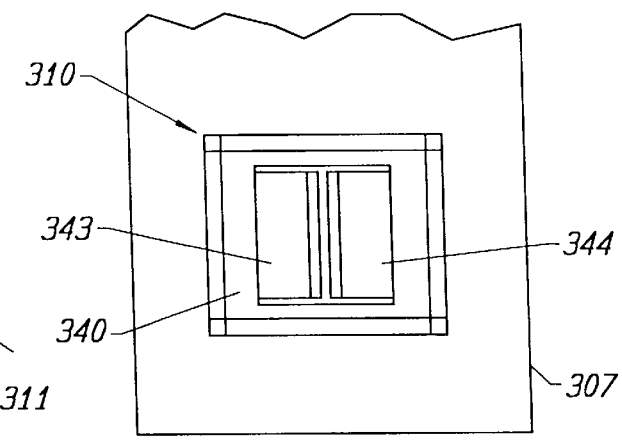
FIG. 3F
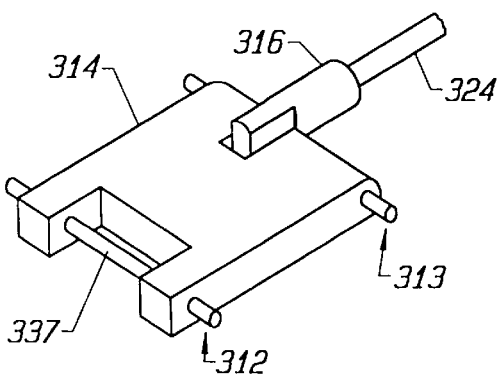
FIG. 3D
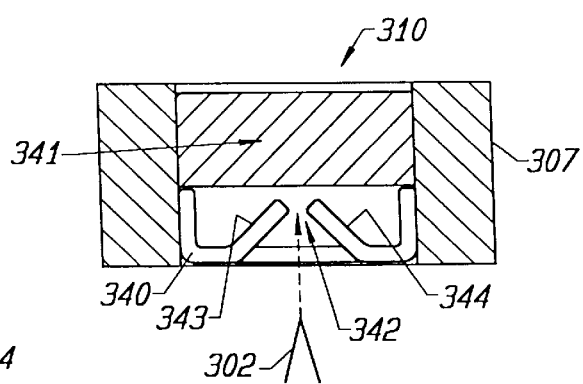
FIG. 3G
FIG. 3E

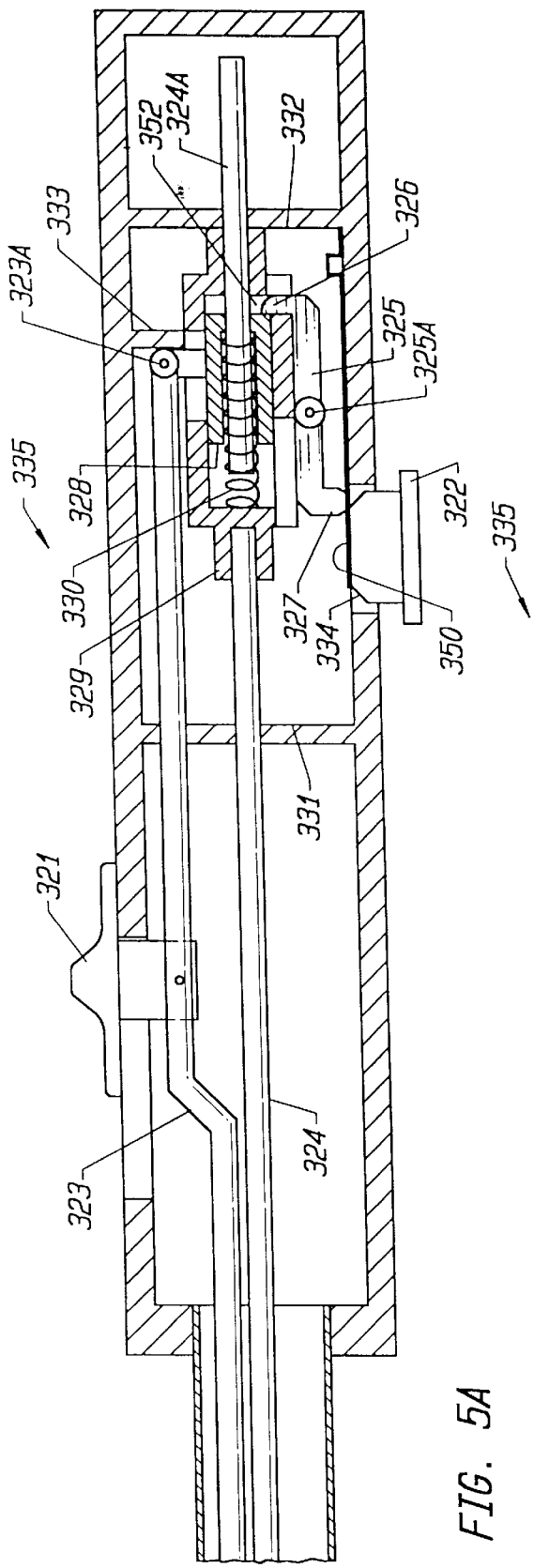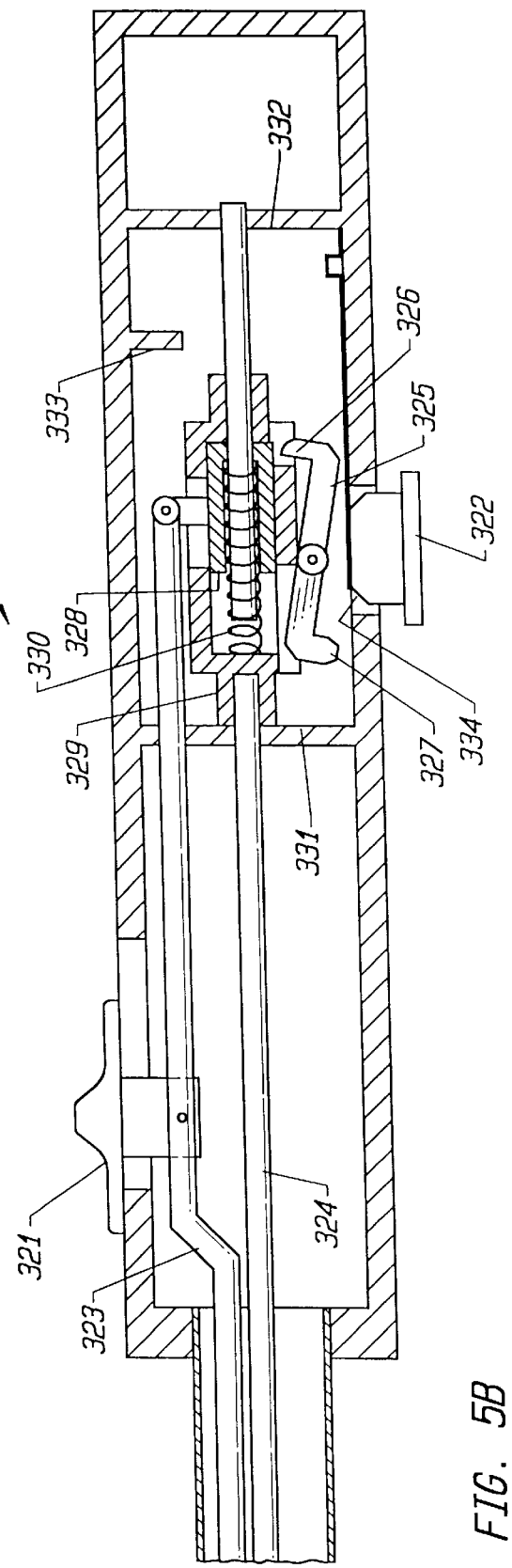

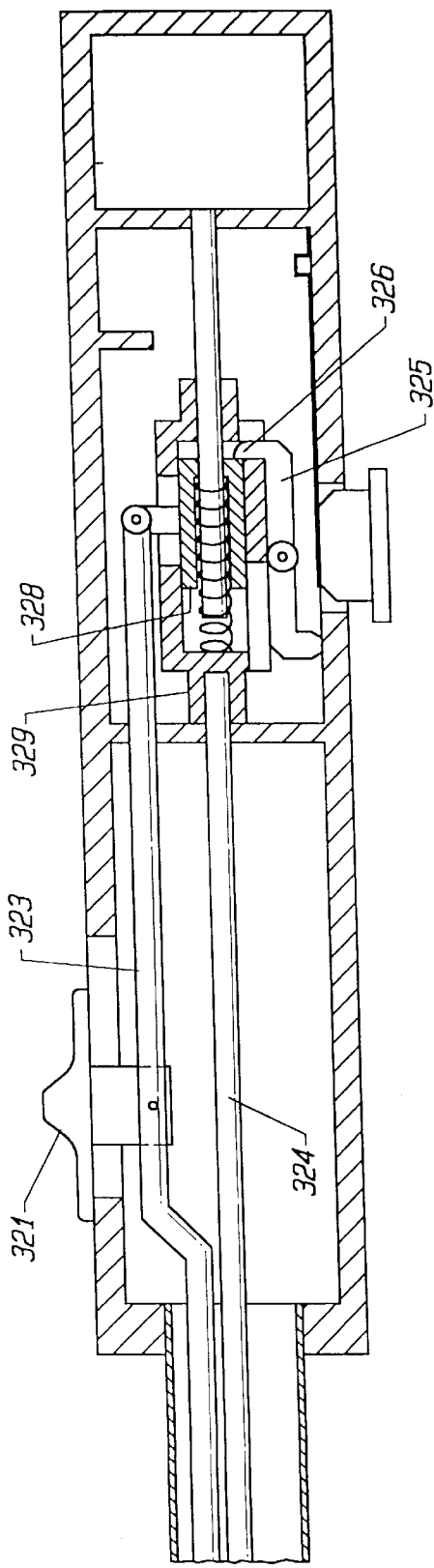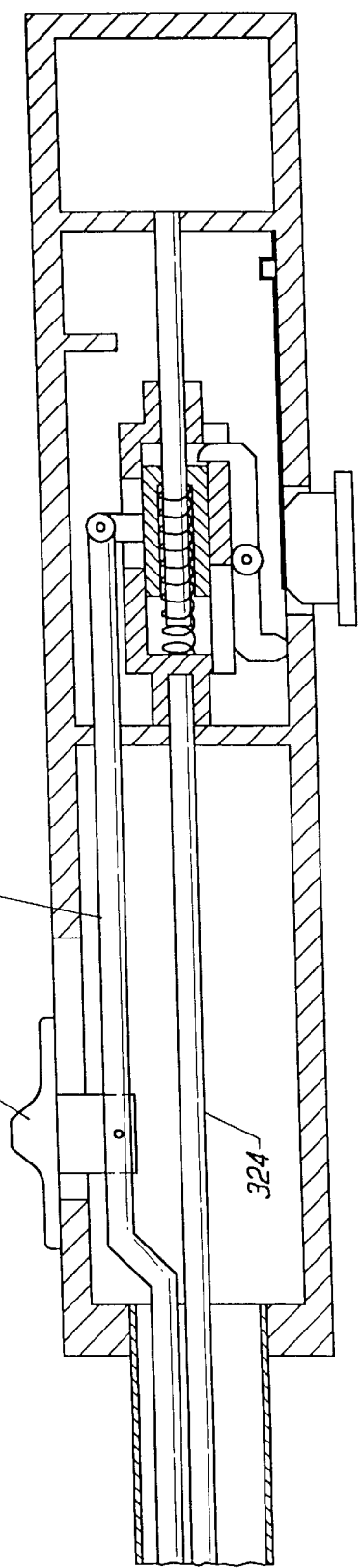
FIG. 5C
FIG. 5D

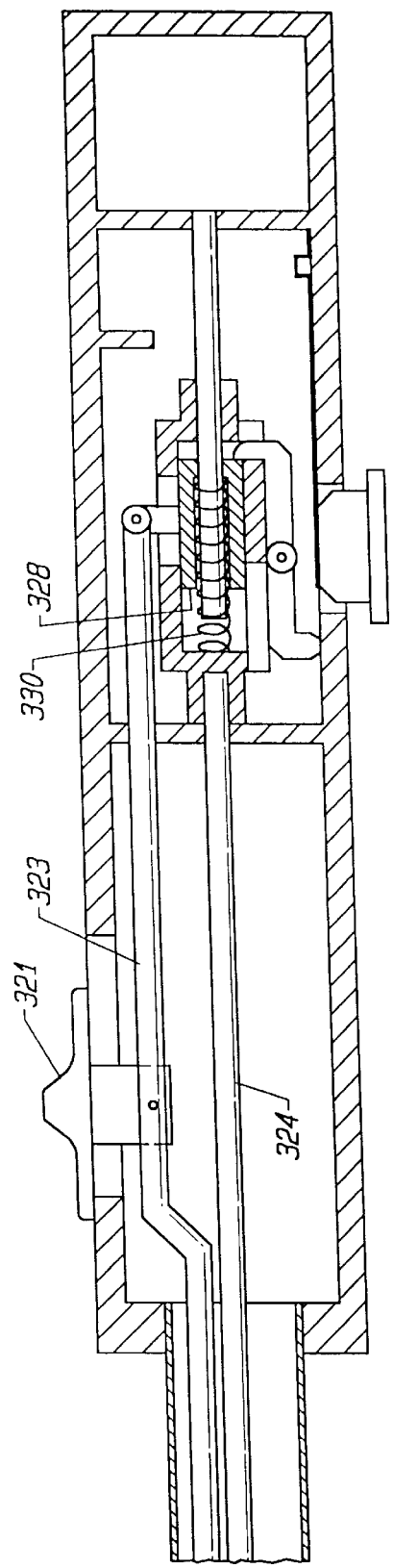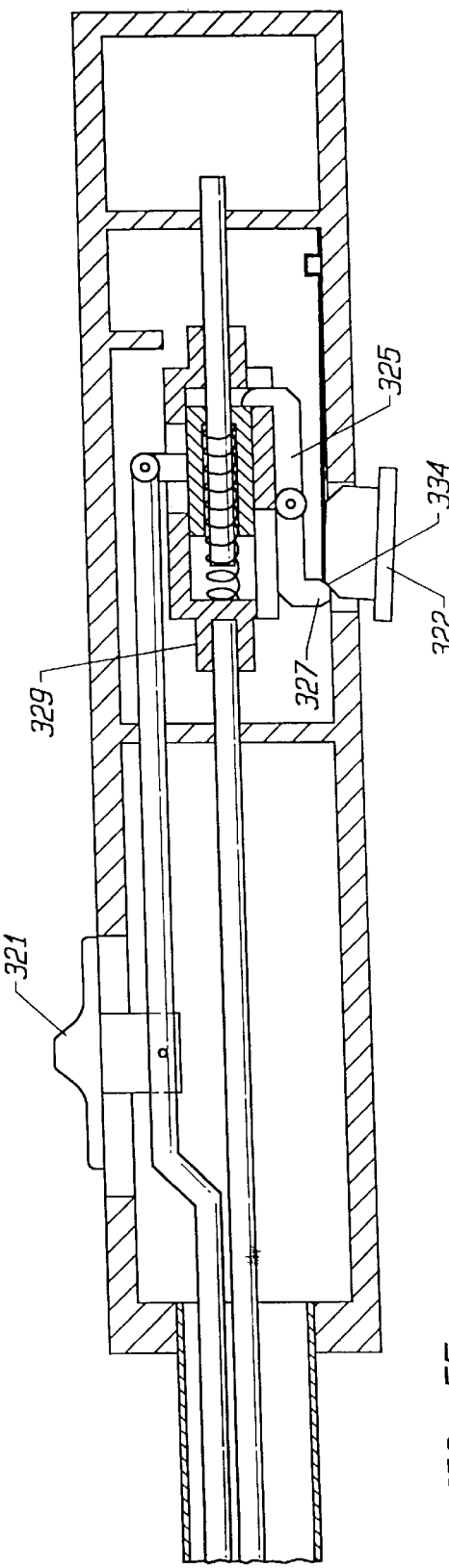
FIG. 5E
FIG. 5F

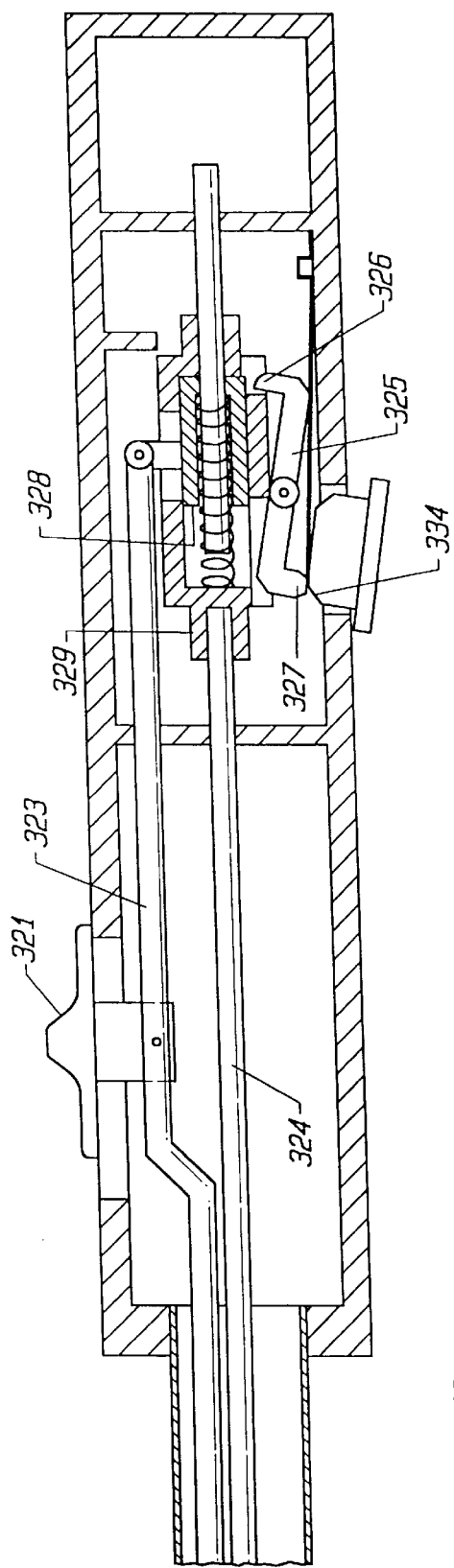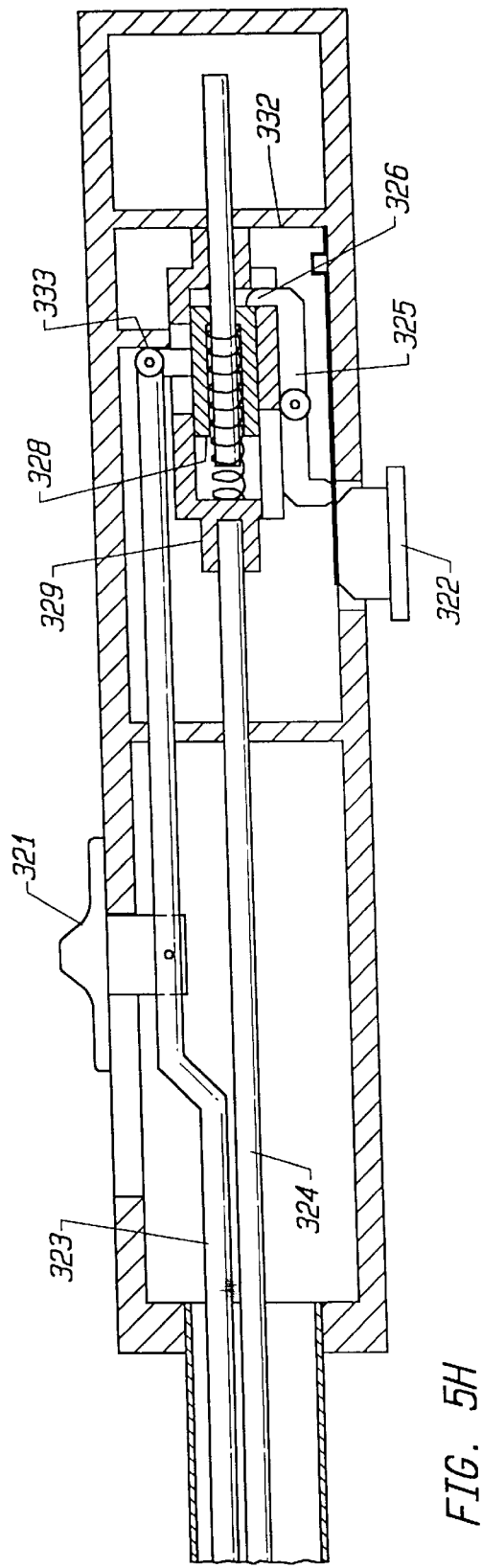
FIG. 5G
FIG. 5H

SUTURED STAPLE SURGICAL FASTENERS, INSTRUMENTS AND METHODS FOR MINIMALLY INVASIVE VASCULAR AND ENDOSCOPIC SURGERY

CROSS REFERENCE TO RELATED APPLICATIONS

The present application is related to the following United States Patent Applications, which applications are by the same inventors as the present invention, and which applications are incorporated by reference herein in their entirety:

U.S. patent application Ser. No. 08/781,578, entitled, "Pinned Retainer Surgical Fasteners, Instruments and Methods for Minimally Invasive Vascular and Endoscopic Surgery", filed on Jan. 9, 1997, and currently pending; and U.S. patent application Ser. No. 08/781,577, entitled, "Ferruled Loop Surgical Fasteners, Instruments, and Methods for Minimally Invasive Vascular and Endoscopic Surgery", filed on Jan. 9, 1997, and currently pending.

FIELD OF INVENTION

This invention relates to the field of devices, instruments and methods for arterial replacement or bypass grafting by minimally invasive (or endoscopic) peripheral vascular and cardiovascular surgery.

BACKGROUND OF INVENTION

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trochar, which is a pointed, piercing device, is delivered into the body with a cannula. After the trochar pierces the abdominal or thoracic wall, it is removed and the cannula is left with one end in the body cavity, where the operation is to take place, and the other end opening to the outside. A cannula has a small inside diameter, typically 5–10 millimeters, and sometimes up to as much as 20 millimeters. A number of such cannulas are inserted for any given operation.

A viewing instrument, typically including a miniaturized video camera, is inserted through one of these cannulas and a variety of surgical instruments and retractors are inserted through others. The image provided by the viewing device may be displayed on a video screen or television monitor, affording the surgeon enhanced visual control over the instruments. Because a commonly used viewing instrument is called an "endoscope," this type of surgery is often referred to as "endoscopic surgery." In the abdomen, endoscopic procedures are commonly referred to as laparoscopic surgery, and in the chest, as thoracoscopic surgery. Abdominal procedures may take place either inside the abdominal cavity (in the intraperitoneal space) or in a space created behind the abdominal cavity (in the retroperitoneal space). The retroperitoneal space is particularly useful for operations on the aorta and spine.

Minimally invasive surgery has virtually replaced open surgical techniques for operations such as cholecystectomy and anti-reflux surgery of the esophagus and stomach. This has not occurred in either peripheral vascular surgery or cardiovascular surgery. An important type of vascular surgery is to replace or bypass a diseased, occluded or injured artery. Arterial replacement or bypass grafting has been performed for many years using open surgical techniques and a variety of prosthetic grafts. These grafts are manufactured as fabrics (often from Dacron or Teflon) or are prepared as autografts (from the patient's own tissues) or heterografts (from the tissues of animals). A graft can be joined to the involved artery in a number of different positions, including end-to-end, end-to-side, and side-to-side. This attachment between artery and graft is known as an anastomosis. Constructing an arterial anastomosis is technically challenging for a surgeon in open surgical procedures, and is almost a technical impossibility using minimally invasive techniques.

Many factors contribute to the difficulty of performing arterial replacement or bypass grafting. See generally, Wylie, Edwin J. et al., Manual of Vascular Surgery, (Springer-Verlag New York), 1980. One such factor is that the tissues to be joined must be precisely aligned with respect to each other to ensure the integrity and patency of the anastomosis. If one of the tissues is affixed too close to its edge, the suture can rip through the tissue and impair both the tissue and the anastomosis. Another factor is that, even after the tissues are properly aligned, it is difficult and time consuming to pass the needle through the tissues, form the knot in the suture material, and ensure that the suture material does not become tangled. These difficulties are exacerbated by the small size of the artery and graft. The arteries subject to peripheral vascular and cardiovascular surgery typically range in diameter from several millimeters to several centimeters. A graft is typically about the same size as the artery to which it is being attached. Another factor contributing to the difficulty of such procedures is the limited time available to complete the procedure. The time the surgeon has to complete an arterial replacement or bypass graft is limited because there is no blood flowing through the artery while the procedure is being done. If blood flow is not promptly restored, sometimes in as little as thirty minutes, the tissue the artery supplies may experience significant damage, or even death (tissue necrosis). In addition, arterial replacement or bypass grafting is made more difficult by the need to accurately place and space many sutures to achieve a permanent hemostatic seal. Precise placement and spacing of sutures is also required to achieve an anastomosis with long-term patency.

Highly trained and experienced surgeons are able to perform arterial replacement and bypass grafting in open surgery using conventional sutures and suturing techniques. A suture has a suture needle that is attached or "swedged on" to a long, trailing suture material. The needle must be precisely controlled and accurately placed through both graft and artery. The trailing suture material must be held with proper tension to keep the graft and artery together, and must be carefully manipulated to prevent the suture material from tangling. In open surgery, these maneuvers can usually be accomplished within the necessary time frame, thus avoiding the subsequent tissue damage (or tissue death) that can result from prolonged occlusion of arterial blood flow.

The difficulty of suturing a graft to an artery using minimally invasive surgical techniques has effectively prevented the safe use of this technology in both peripheral vascular and cardiovascular surgical procedures. When a minimally invasive procedure is done in the abdominal cavity, the retroperitoneal space, or chest, the space in which the operation is performed is more limited, and the exposure to the involved organs is more restricted, than with open surgery. Moreover, in a minimally invasive procedure, the instruments used to assist with the operation are passed into the surgical field through cannulas. When manipulating instruments through cannulas, it is extremely difficult to position tissues in their proper alignment with respect to each other, pass a needle through the tissues, form a knot in the suture material once the tissues are aligned, and prevent the suture material from becoming tangled. Therefore, although there have been isolated reports of vascular anastomoses being formed by minimally invasive surgery, no system has been provided for wide-spread surgical use which would allow such procedures to be performed safely within the prescribed time limits.

As explained above, anastomoses are commonly formed in open surgery by suturing together the tissues to be joined. However, one known system for applying a clip around tissues to be joined in an anastomosis is disclosed in a brochure entitled, "VCS Clip Applier System", published in 1995 by Auto Suture Company, a Division of U.S. Surgical Corporation. A clip is applied by an applying instrument about the tissues in a nonpenetrating manner, i.e., the clip does not penetrate through the tissues, but rather is clamped down around the tissues. As previously explained, it is imperative in forming an anastomosis that tissues to be joined are properly aligned with respect to each other. The disclosed VCS clip applier has no means for positioning tissues. Before the clip can be applied, the tissues must first be grasped and properly positioned with respect to each other, for example by skewering the tissues with a needle as in common suturing techniques and/or with forceps to bring the tissues together. As discussed, it is extremely difficult to perform such positioning techniques in minimally invasive procedures. Therefore, there is currently a need for a system adapted for wide-spread surgical use that is capable of manipulating and positioning tissues in proper alignment with respect to each other, and thereafter capable of forming an anastomosis in minimally invasive procedures.

SUMMARY OF THE INVENTION

In view of the foregoing, it is an advantage of the invention to provide surgical staples, that permit surgeons to perform peripheral vascular and cardiovascular surgery with minimally invasive techniques.

It is an advantage of this invention to provide surgical staples useful in minimally invasive procedures to replace or bypass a diseased, occluded or injured artery quickly, safely, and reliably.

It is an advantage of the invention to provide surgical staples useful in constructing an artery to graft anastomosis in the abdominal cavity, retroperitoneal space or chest.

It is an advantage of the invention to provide instruments and methods for precisely manipulating the staples and for applying the staples by minimally invasive surgery.

It is an advantage of the invention to provide staples, instruments and methods that permit surgeons to perform minimally invasive surgery by employing many of the same suturing skills and techniques they use in open surgery.

It is an advantage of this invention to provide surgical staples and instruments to hold and form them. Such staples and instruments enable other soft tissue anastomoses to be constructed and tissues to be joined together in the chest, retroperitoneum, or abdomen by minimally invasive techniques.

It is an advantage of the invention to provide surgical staples and instruments that are also capable of performing these procedures during traditional open surgery.

These and other advantages are achieved by providing a surgical staple and an instrument for applying this staple. The staple of the invention is designed to permit surgeons to construct vascular anastomoses, other soft tissue anastomoses, and to join together other soft tissues by minimally invasive surgery, while employing many of the same skills and techniques that are applicable to manipulating conventional suture needles and to constructing such anastomoses with conventional sutures. The invention, however, allows these procedures to be done in a knotless and sutureless fashion. The staple according to a preferred embodiment includes a base integrally formed with a pin and a flange on opposed sides of the base. A needle composed of a narrow shaft and a piercing tip is initially attached to the pin of the staple. Embodiments of the present invention further include an instrument for holding the staple and needle, and for manipulating the needle to pierce and control a graft and artery with the same sewing techniques surgeons commonly use in traditional open surgery.

After the graft and artery have been pierced and brought into close proximity on the pin of the staple, additional mechanisms initially provided in a retracted position within the instrument are driven forward to remove the needle from the staple, and to bend the pin and flange down over the base to form a completed staple around the tissues being fastened together. As used herein, the term "unformed staple" refers to the staple prior to the pin and flange being bent down over the base. The term "completed staple" refers to the staple after the pin and flange have been bent down over the base to fasten the tissues of the anastomosis together. Once the completed staple has been formed, the staple is detached from the applying instrument, leaving behind an implanted surgical fastener that attaches the graft and the artery together. These staples, together with the apparatus and methods to use them, when applied in sequence around the junction between an artery and graft, permit a vascular anastomosis to be created using minimally invasive techniques.

While the invention is designed primarily for minimally invasive arterial grafting, the invention is also useful for attaching together a variety of other non-vascular soft tissues in the chest, retroperitoneal space or abdomen by minimally invasive techniques. For example, the invention may be used to construct an anastomosis in the stomach, intestine, or colon, or to perform any of the standard anti-reflux operations involving the stomach, esophagus, or diaphragmatic hiatus. The staples and instruments of the invention may also be used in an open surgical procedure.

BRIEF DESCRIPTION OF THE DRAWINGS

The above and other advantages of the present invention will be apparent upon consideration of the following detailed description, taken in conjunction with the accompanying drawings, in which like reference characters refer to like parts throughout, and in which:

FIG. 3C shows a perspective view of the needle removal member of the instrument;

FIG. 3D shows a perspective view of the staple forming member of the instrument;

FIG. 3E shows a perspective view of the carriage component of the instrument;

FIG. 3F shows a plan view of the gripping end of the needle removal member of FIG. 3C with a gripper;

FIG. 3G depicts an end view, in section, of the gripping end of the needle removal member with its gripper;

FIGS. 5A–5H show how the controls and mechanisms of the handle end of the instrument drive the distal end staple forming assemblies;

DETAILED DESCRIPTION OF THE INVENTION

Embodiments of the present invention relate to a sutured staple surgical fastener for fastening together an artery and a graft, and methods and apparatus for applying the fastener. In a preferred embodiment of the present invention, the fastener may be applied in a minimally invasive surgical procedure, utilizing suturing techniques commonly applied in open surgical procedures. It is also contemplated that the present invention may be used in open surgical procedures. As explained in greater detail below, the sutured staple surgical fastener according to the present invention may be applied by a hand-held instrument manually or automatedly controlled by a surgeon, or alternatively, the fastener may be applied by a remotely controlled robotic mechanism. Furthermore, although a preferred embodiment of the invention is used to fasten together a vascular artery and a graft, it is understood that the present invention may be used to fasten together tissues, or a tissue and graft, in any surgical procedure where tissues or tissue and graft are to be fastened together. As used herein, the term "tissue" may refer to any vascular passage or other body organ, and the term "graft" may refer to any biological or synthetic graft.

Figure 1A:
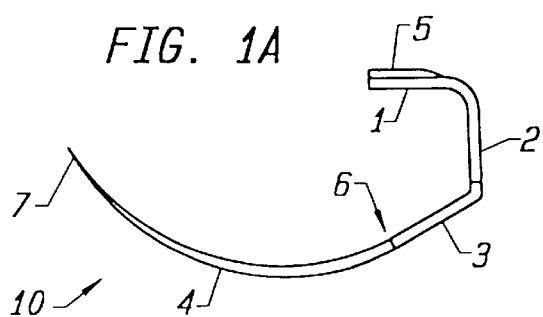
FIG. 1A shows an elevation (or side) view of an illustrative staple of the invention prior to application.
Figure 1B:
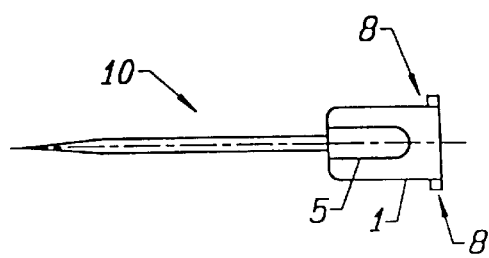
FIG. 1B shows a plan (or top) view of the staple shown in FIG. 1A.
Figure 1C:
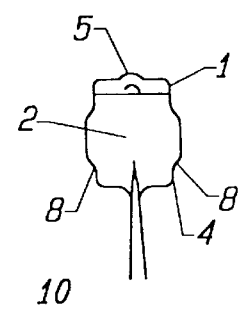
FIG. 1C shows an end view, looking from left to right, of the open staple as shown in FIG. 1A.

Referring now to FIGS. 1A–1C, there is shown an unformed surgical staple 10 comprising a flange 1, a base 2, and a pin 3. A needle 4 is affixed to pin 3 of the unformed staple 10. In general, the tissues to be fastened together are skewered onto needle 4 and positioned on pin 3. Thereafter, needle 4 is cut or otherwise detached from the unformed staple 10 at a disengagement point 6. After the needle is removed, pin 3 is bent over base 2, and flange 1 is then bent over pin 3 and over portions of the graft and artery immediately adjacent to pin 3 to form a completed staple and secure together the tissues to be joined.

Base 2 preferably includes a substantially planar surface having edges defining a substantially rectangular or square shape. It is understood that base 2 may include edges defining a variety of other shapes in alternative embodiments of the invention. Similarly, flange 1 includes a corresponding, substantially planar surface with edges defining an approximate rectangular or square shape. The edges of flange 1 may vary in alternative embodiments to substantially match that of base 2. In an unbent position, the flange 1 and base 2 are preferably oriented at an angle of less than 180° with respect to each other, and optimally about 90° with respect to each other. The planar surfaces of the flange 1 and base 2 cooperate with each other upon formation of the completed staple to secure the artery, graft, or other such tissues together. In arterial grafting, the base may contact either the graft or the artery, and the flange may contact the other of the graft or artery on the other side of the anastomosis. The positions of the artery and graft may be reversed relative to the base and flange in an alternative embodiment of the invention. Base 2 preferably also includes wings 8 to facilitate releasable gripping of the staple 10 by the staple applying instrument as explained hereinafter.

The corresponding planar surfaces of the base and flange are large enough so that the force applied to the graft and artery by the completed staple effectively secures the artery and graft together, preferably achieving a substantially hemostatic seal. The force applied by the completed staple must not be so large that it interferes with the natural, biological processes that support the health of the tissues, including the movement of fluids, nutrients, oxygen, etc. within those tissues. When using the staple to join an artery and graft, the needle creates a hole in the artery as it is driven through the vessel. Even if that hole is substantially larger than the shaft to the needle, sufficient force is exerted by the base and flange on the artery and graft to prevent any significant leakage of blood from the artery through the hole. Following bending of the pin and flange, the planar surfaces of the base and flange are substantially parallel to each other. However, it is not necessary that the planar surfaces of the base and flange be parallel to each other in alternative embodiments, with the provision that the planar surfaces provide an appropriate amount and distribution of force on the tissues to be fastened. After the staple is formed, the separation between the flange and the base remains substantially constant.

The separation or gap between the flange and the base, and therefore the amount of pressure exerted on the tissues that are contained therebetween, is adjustable depending on the bend points designed into the pin and the flange. As would be appreciated by those skilled in the art, the bend points in the pin and flange may be controlled by forming the bend points of the pin and flange with a slightly thinner cross-sectional area than adjacent portions of the pin and flange. Alternatively, the bend points may be formed with a slightly lower modulus than adjacent areas. In this way, upon application of the bending force, the pin and flange win bend at predetermined and controllable point.

Base 2 preferably has a minimum distance from any one edge to the opposite edge of between about 0.03 to 0.25 inches, depending on the nature, thickness and location of the tissues to be joined. The base 2 may also have a surface area to contact structures to be fastened together between about 0.01 and 0.2 square inches. The planar surface of the flange preferably has a shape and surface area substantially corresponding to that of the planar surface of the base.

As shown in FIG. 1A, pin 3 preferably forms an angle of less than 180° with the base 2. As indicated, the completed staple 10 is formed only after the appropriate tissues or grafts have been skewered by the needle 4 and advanced onto pin 3. With the tissues or graft trapped on the pin, the needle is removed, and formation of a completed staple begins by first bending the pin 3 with the tissues skewered thereon down over base 2, and then bending the flange 1 over the pin 3. In order to accommodate the pin 3, flange 1 preferably includes a recess 5 sized to receive all or a portion of the diameter of the pin after bending. Pin 3 is bent to lie substantially horizontally on top of a graft or artery. In embodiments of the invention where the recess 5 is sized to receive only a portion of the diameter of pin 3, the portion of pin 3 not residing within recess 5 win sink into the artery or graft due to the compliancy of the artery and graft. This allows the planar surface of flange 1 to more evenly distribute the fastening force of the staple on the artery and graft.

Needle 4 in general may be used to pierce a graft at a selected location, move the graft to a position near an artery, and then pierce the artery at a selected location to precisely and correctly align the graft and the artery for connection by the completed staple. Needle 4 is preferably made of a biocompatible material, and may be provided with a wide range of shapes, from straight to highly curved, and a variety of different sizes. Such needles are known in the art. In preferred embodiments of the invention, the needle is provided with substantially the same range of piercing points, curvatures and sizes as commercially available suture needles used with sizes 2-0 to 8-0 sutures. This range of piercing points, shapes and sizes permits the surgeon to use essentially the same suturing (or sewing) motions that are commonly used with conventional suture needles in open surgical procedures, and allows this invention to be used in a wide range of tissue fastening applications. The precise configuration of the needle may vary, depending on, for example, the anatomy of the patient, the geometry of the surgical set-up, the area of the body in which the fasteners are to be applied, and the nature, type and thickness of the tissues that are to be joined together.

The needle must also be strong enough to withstand the forces encountered as the needle is driven through the tissues and/or graft. The needle includes a tip 7 adapted to pierce or otherwise penetrate the structures to be joined. The tip 7 is shaped into a point designed to penetrate tissues without injuring, tearing, or otherwise affecting the integrity of the tissue. This is largely accomplished by forming tip 7 with a substantially circular, elliptical, or oblong cross-section, substantially free of a cutting edge. It is understood, however, that needle 4 may have a tip 7 with a cutting edge along its length in alternative embodiments of the invention. Tip 7 of needle 4 may either taper to a point or have a blunt end, depending, for example, on whether the needle is passing through a normal and relatively undiseased artery, a calcified or artrosclerotic artery, or a thinned out, endarterectornized artery. A blunt tip needle may be preferable for use when a surgeon first needs to make a hole in the artery, or other tissue, with a punch. A blunt tip needle could then penetrate through this pre-punched hole. Such a procedure may be preferable in cases involving a severely calcified artery.

Figure 1D:
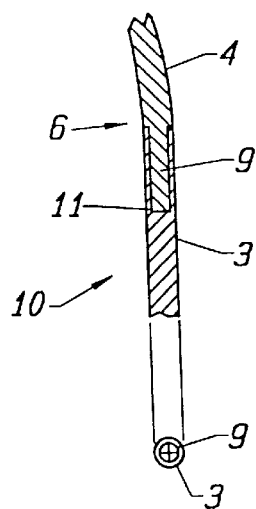
FIG. 1D shows an elevation view and an end view of a peg and cup coupling between a staple's needle and the remaining portions of the staple.

As stated, once the tissues or tissue and graft have been skewered and are located on pin 3, needle 4 is removed from the unformed staple at a disengagement point 6. In a preferred embodiment of the invention, the needle is formed separately from other portions of the staple, and then "swedged on" or otherwise removably attached to the pin. In this form, the needle may be pulled off the pin once the tissues are positioned on the pin. Such an example is shown in FIG. 1D, in which needle 4 includes a peg 9, and pin 3 may include a cup 11 for receiving the peg 9. The peg 9 fits within the cup 11 and is frictionally held therein to removably attach the needle to the pin. The peg 9 and cup 11 may respectively include corresponding flat surfaces that mate with each other to prevent rotation of the needle 4 relative to the pin 3. It is understood that the positions of the cup 11 and peg 9 may be reversed relative to the pin and needle in an alternative embodiment of the invention. It is further understood that the mechanism for removably attaching needle 4 to pin 3 may be formed of varying configurations, with the provision that the size of the joint between the needle and pin not be substantially larger than portions of the needle and pin adjacent to the joint. In an alternative embodiment of the invention, the needle and pin may be manufactured as an integral part of the staple. In this case, the needle needs to be cut off and removed before the staple is closed. A tool for cutting off the needle is disclosed in U.S. patent application Ser. No. 08/781,578, previously incorporated herein by reference.

The staple is preferably constructed of any biocompatible material having sufficient malleability and strength for insertion through a graft, through an artery (even if calcified), or through other soft tissues in the chest, abdominal cavity, or retroperitoneum, and for retaining its structural integrity after the pin and flange have been bent. Preferably, the staple is made of non-absorbable, biocompatible metals, such as stainless steel, tungsten or titanium. They may also be made of non-absorbable plastics, such as Teflon or nylon, or biodegradable polymers, such as polyglycolic acid. For artery-to-graft anastomoses, a non-absorbable staple is needed. However, absorbable staples may be used if appropriate to the clinical situation (such as joining certain soft tissues together temporarily or constructing anastomoses in the stomach, intestine, or colon). If clinical application requires an absorbable staple, then the staple may be made of a bioabsorbable material.

Figure 2A:
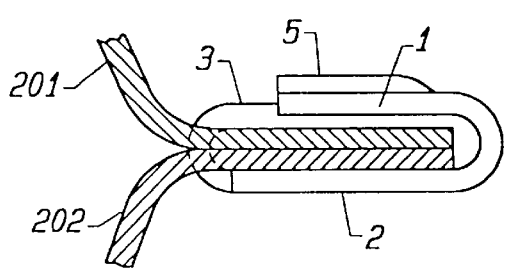
FIG. 2A shows an elevation view of a closed staple attaching an artery and graft.
Figure 2C:
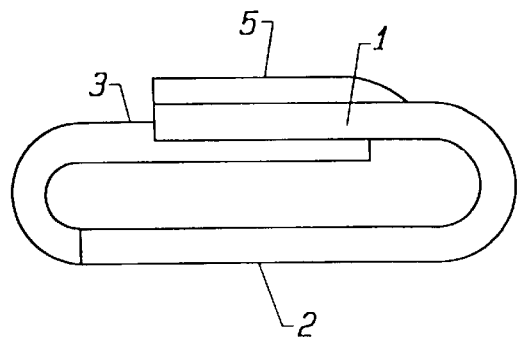
FIG. 2C shows the closed staple of FIG. 2A without an attached artery and graft.

FIG. 2A shows a completed staple 10 fastening together an artery 201 and a graft 202. The graft and artery are held together on the pin 3 by the cooperation of the planar surfaces of the flange 1 on one side and the base 2 on the other. The pin remains interlocked with the graft and artery after application. The pin acts in place of a conventional suture material, while the planar surfaces of the base and flange spread the forces holding the graft and artery together over a much larger area than is possible with a conventional suture. This results in less tendency for the staple to cut through either the graft, artery, or other tissue being joined together than is the case with virtually any suture material. These planar surfaces of the base and flange also assist in providing a hemostatic seal between the graft and artery by securing them together over a larger area than is possible with a conventional suture. After application, the completed staple 10 remains in place at the surgical site as what becomes an implanted surgical staple. FIG. 2C shows the completed staple of FIG. 2A without the artery 201 or graft 202.

Figure 2B:
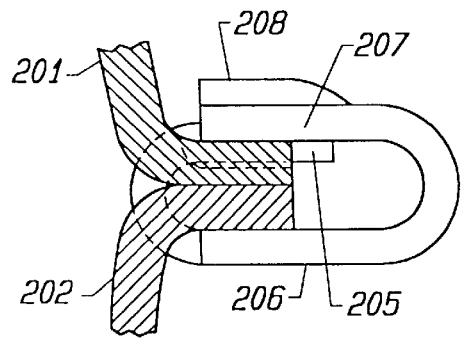
FIG. 2B shows an elevation view of a smaller closed staple attaching an artery and graft.
Figure 2D:
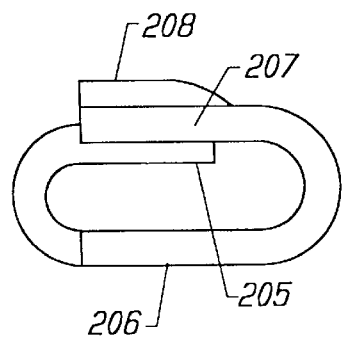
FIG. 2D depicts the smaller closed staple of FIG. 2B without an attached artery and graft.

FIG. 2B shows another example of the completed staple (with a shorter pin 205, flange 207 and base 206) attaching an artery 201 and graft 202. This figure shows the compliancy of artery 201 causing the portion of pin 205 not enclosed by recess 208 to sink into the artery 201 and thereby allow the planar surface of flange 207 to distribute the fastening force of the staple around the portion of artery 201 in contact with staple 10. FIG. 2D shows the staple of FIG. 2B without the artery 201 or graft 202.

Figure 2E:
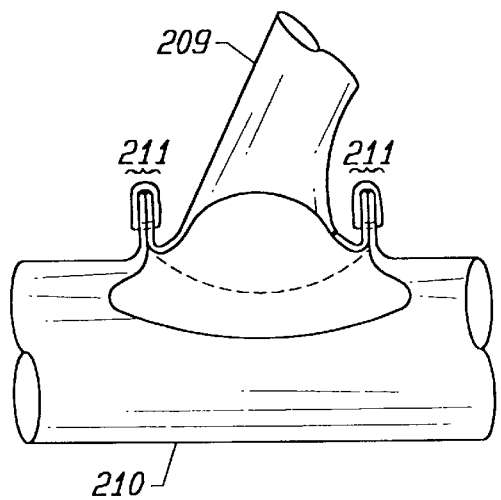
FIG. 2E is a schematic drawing, not to scale, illustrating the use of the staple of FIG. 1 to form a graft-to-artery anastomosis.

FIG. 2E shows an illustrative use of the surgical staple in accordance with the principles of the present invention. A graft 209 is joined to an artery 210 using a pair of staples 211 (identical to staple 10). Once the needle 4 has skewered first the graft 209 then the artery 210, or first the artery 210 and then the graft 209, the needle is removed and the pin and flange are folded over the base to thereby form the completed staple. A plurality of such staples may be applied around the circumference of the graft to form the anastomosis. In a preferred embodiment, the staple 10/211 is a vascular fastener, and most preferably an arterial fastener. However, it is contemplated that the fastener according to the present invention may be used to attach a variety of non-vascular soft tissues together, such as for example, in the abdominal cavity, the retroperitoneal space or in the chest. In each case, the soft tissues to be joined together are skewered onto the needle, located on the pin, the needle is removed, and thereafter the pin and flange are folded down over the base to form the completed staple. Because the staple may be used with various sizes and configurations of arteries, grafts, and other tissues, the size of the staple will vary depending on the intended application. This will include both the width and length of the flange and base, as well as the gap or separation between the base and the flange in the completed staple.

Figure 2F:
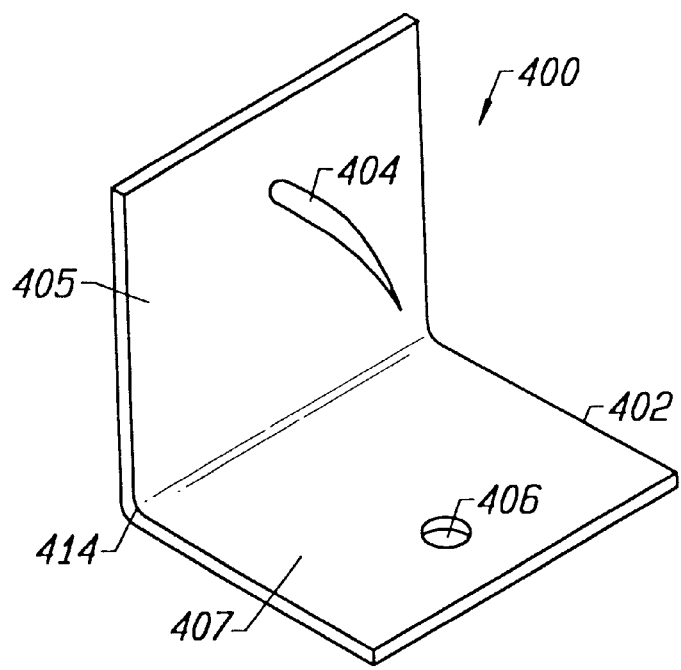
FIGS. 2F–2H are perspective and side views of a staple according to an alternative embodiment of the present invention.
Figure 2G:
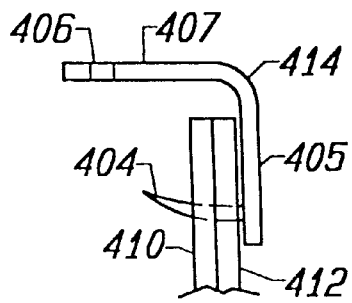
Figure 2H:
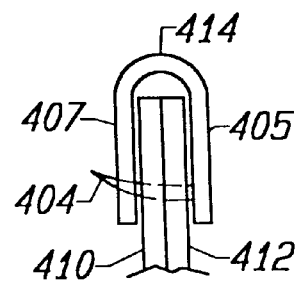

A staple 400 according to an alternative embodiment of the invention is shown in FIGS. 2F–2H. The staple 400 comprises a single angled member 402 having a needle 404 affixed to one angled section 405, and a hole 406 in another angled section 407. In operation, the staple 400 may be gripped by a staple holder member described hereinafter at either section 405 or 407, and manipulated so that needle 404 skewers the tissues, or graft and tissue, to be joined as previously described. Once tissues 410 and 412 are positioned on the needle 404 as shown in FIG. 2G, the staple 400 may be closed by bending section 407 over section 405. Hole 406 is positioned so as to receive the needle 404 therethrough once the staple is closed, as shown in FIG. 2H. In a completed staple 400, the tissues remain pinned on needle 404, while the sections 405 and 407 act to distribute the forces holding the tissues together over a much larger area than is possible with a conventional suture.

The sections 405 and 407 may be formed from the same materials as staple 10 of FIG. 1A, and may form an angle of less than 180° with respect to each other in an unformed staple. The corresponding planar surfaces of the sections 405 and 407 are large enough so that the force applied to the tissues by the completed staple effectively secures the tissues together, preferably achieving a substantially hemostatic seal. Following bending of the sections 405 and 407, the sections 405 and 407 are substantially parallel to each other. However, it is not necessary that they be parallel to each other in alternative embodiments, with the provision that the sections 405 and 407 provide an appropriate amount and distribution of force on the tissues to be fastened. After the staple is formed, the separation between the sections 405 and 407 remains substantially constant.

The separation or gap between the sections 405 and 407 in a completed staple, and therefore the amount of pressure exerted on the tissues that are contained therebetween, is adjustable depending on the bend section 414 designed into the staple 400. As would be appreciated by those skilled in the art, the width of the bend section determining the spacing between the sections 405 and 407 may be controlled by forming the bend section with one or more portions having a slightly thinner cross-sectional area, or a lower modulus, than portions of the staple 400 adjacent thereto. In this way, upon application of the bending force, the staple 400 will bend in a predetermined and controllable fashion.

Needle 404 may be formed of substantially the same shapes and materials as needle 4 described with respect to FIG. 1A. After the sections 405 and 407 are properly positioned around tissues 410 and 412, the portion of needle 404 protruding through hole 406 may be detached, bent or otherwise deformed to prevent damage by the tip of the needle to tissues surrounding the completed staple. In embodiments where the needle is detached, the needle may either be a single or two-part needle as described above.

Figure 3A:
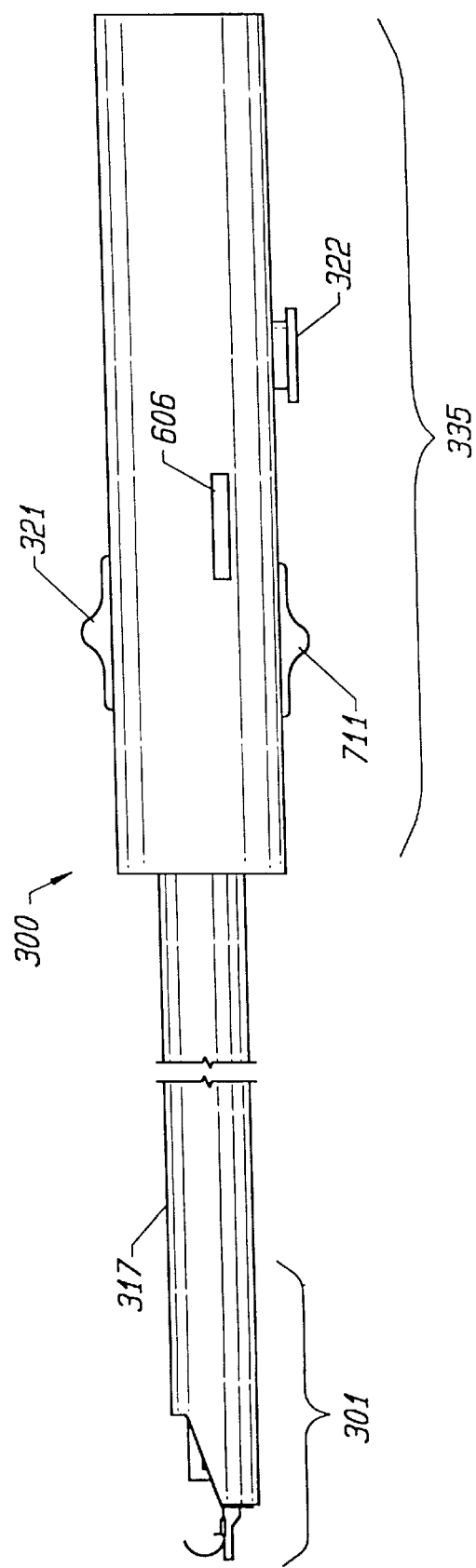
FIG. 3A is an elevation view of an exemplary surgical instrument of applying the staple of FIGS. 1 and 2.

In addition to the staple 10 described above, embodiments of the present invention also include an instrument for applying the staple in either minimally invasive or open surgical procedures. Referring now to FIG. 3A, a staple applying instrument 300 is shown having a distal or working end 301, a proximal or handle end 335, and a shaft 317 between the proximal and distal ends. As explained hereinafter with respect to FIGS. 3A–7F, working end 301 includes a staple holder 308 (FIG. 4A), staple forming member 309, needle removal member 307, and latch plate 705 (FIG. 7A). As further explained hereinafter with respect to FIGS. 3A–7F, the handle end 335 (FIG. 3A) includes control mechanisms for manipulating and controlling the operation of the staple holder 308, the staple forming member 309, the needle removal member 307, and the latch plate 705.

The shaft 317 may be either straight or curved, and is preferably made of a suitable rigid material, such as stainless steel, reinforced plastics, or composite materials, so that a surgeon may precisely control the working end of the instrument during surgery. Preferably, the shaft 317 is about 5–10 millimeters in diameter so that it fits through and may be used with conventional canulas, but it may be as large as about 20 millimeters in diameter. Shaft 317 may have a variety of lengths suitable to particular surgical situations, and is preferably about 15–27 centimeters long. The shaft houses drive rods which couple various controls on handle end 335 with the above-named components in working end 301, thus permitting the staple to be manipulated and completed. The particular size, diameter, length and configuration of the instrument may vary depending on the size and shape of the needle, the geometry of the tissues to be joined, or the artery to be grafted, anatomic variations, and the size of the surgical space and structures on which the surgeon is operating.

Figure 6A:
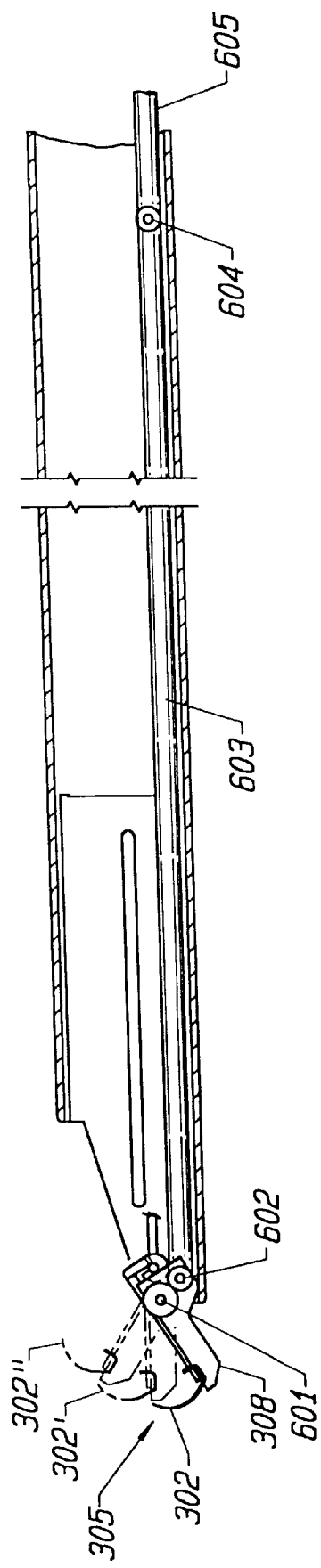
FIG. 6A shows a side view, in section, of the distal end of the staple instrument with the staple holder member shown.
Figure 6B:
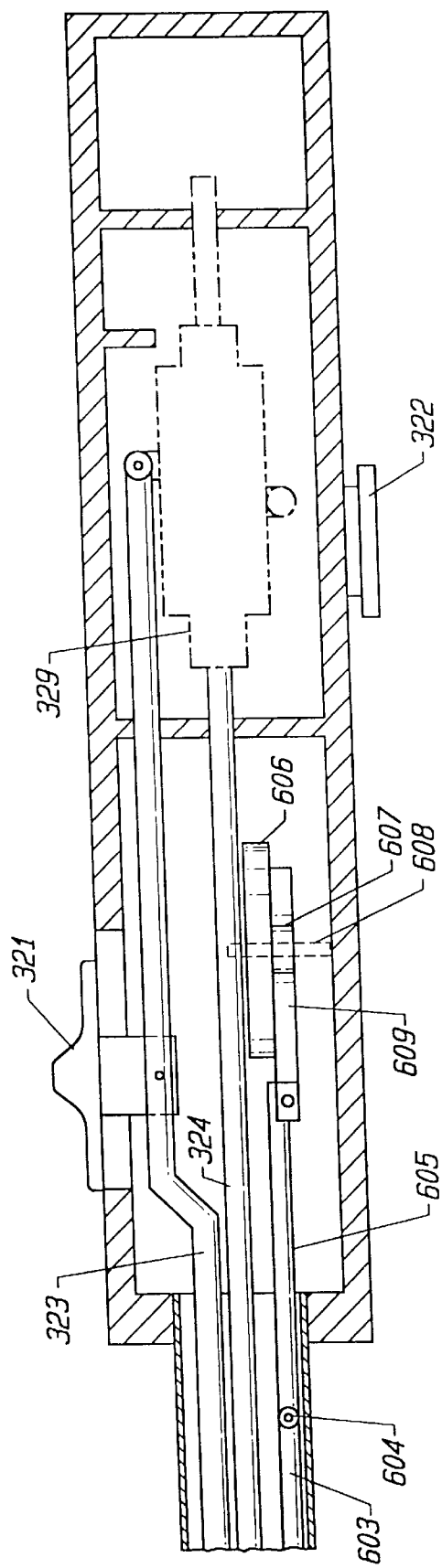
FIG. 6B shows a side view, in section, of the handle end of the staple instrument with the corresponding controls for articulation shown.
Figure 7A:
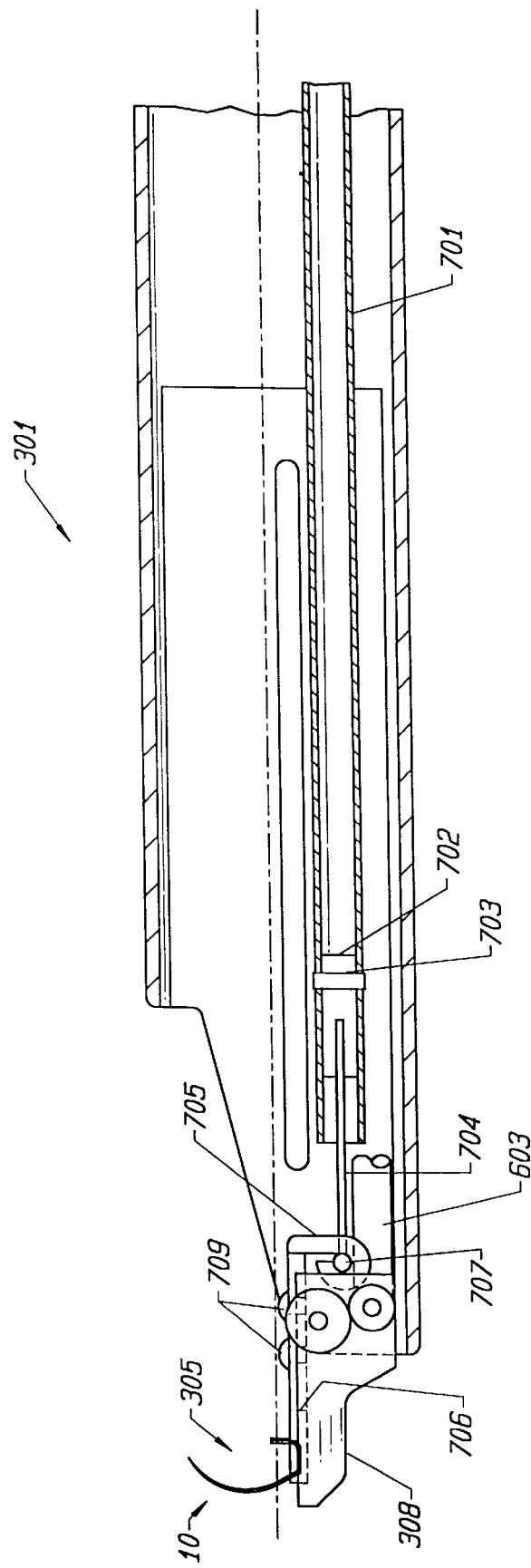
FIG. 7A shows a side view, in section, of the distal end of the staple instrument with the staple latching assembly shown.

Referring now to FIGS. 6A and 6B, distal end 301 includes a staple holder 308 for firmly but releasably gripping base 2 of an unformed staple 305 (which is identical to staple 10 shown in FIG. 1A), and for pivoting staple 305 with one degree of freedom relative to the shaft 317. In a preferred embodiment, the staple holder may articulate at least 90°. However, specific surgical procedures may employ either larger or smaller ranges of motion. The elongated shaft of the instrument allows the surgeon to rotate the instrument about the longitudinal axis of the instrument. These features provide the surgeon with a wide range of freedom to orient the needle relative to the tissues to be skewered and joined together.

Figure 7B:
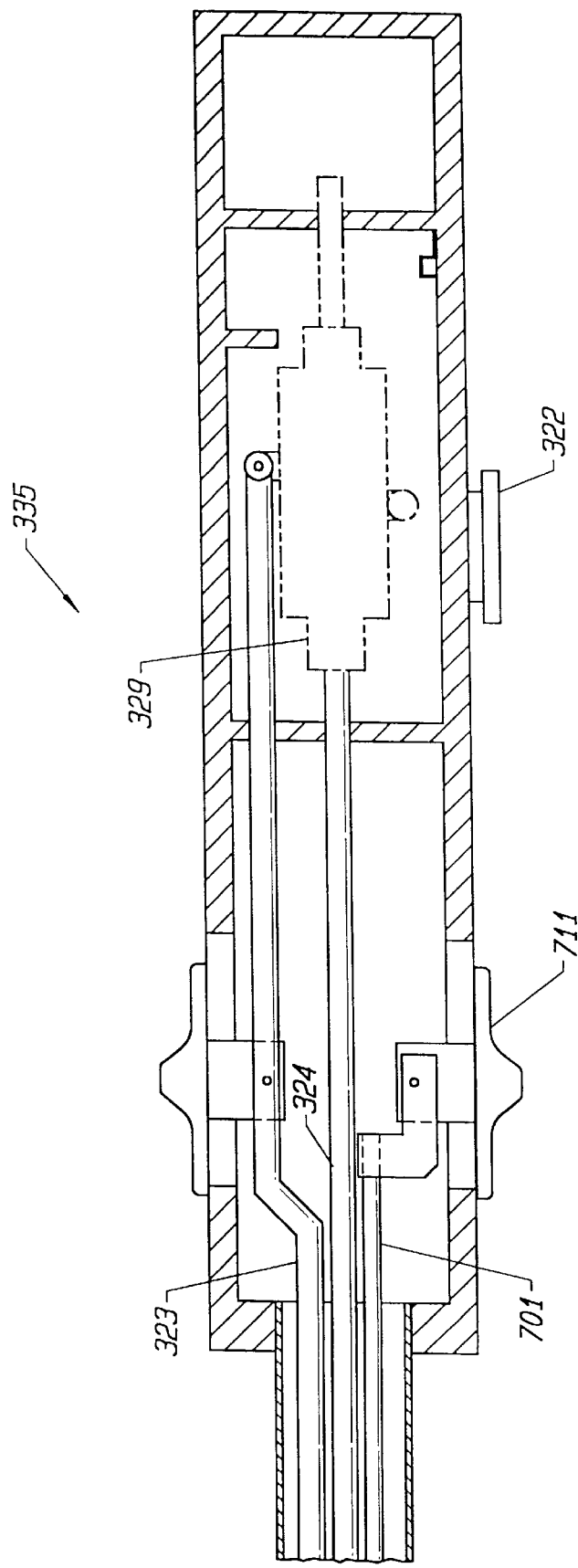
FIG. 7B shows a side view of the handle end of the staple instrument with the corresponding controls for latching shown.
Figure 7C:
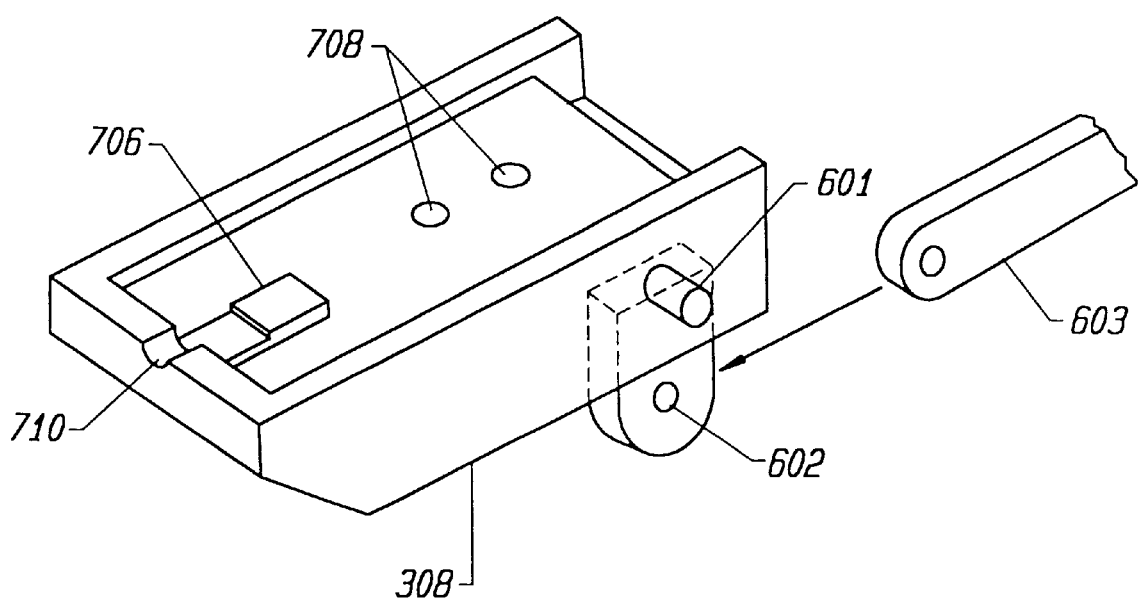
FIG. 7C shows a perspective view of the staple holder member.

In operation, prior to insertion of the instrument to the surgical site, base 2 of staple 305 (FIG. 7A) is securely supported on a backstop 706 (FIGS. 7A and 7C). Thereafter, staple 305 and staple holder 308 may be articulated as follows. As shown in FIG. 6B, handle end 335 includes a thumbwheel 606 for controlled manual rotation by a surgeon. Thumbwheel 606 is mounted on an axle 608 with pinion 607 so that rotation of thumbwheel 606 causes an equivalent rotation of pinion 607. A rack gear 609 is coupled to a drive rod 605, and is juxtaposed between various guides (not shown) so that teeth on rack gear 609 matingly engage with teeth on pinion 607. This rack and pinion assembly converts rotational movement of thumbwheel 606 into longitudinal motion of drive rod 605. In a preferred embodiment, drive rod 605 is pivotally coupled to drive rod 603 via a pin 604 such that drive rod 603 is capable of pivoting with respect to drive rod 605. Drive rod 603 is in turn pivotally coupled to staple holder 308 via pin 602 as shown in FIG. 6A. In an alternative embodiment, pivot point 604 and drive rod 603 may be omitted, and drive rod 605 may extend the entire length of shaft 317 between thumbwheel 606 and staple holder 308. Staple holder 308 is pivotally mounted on an axle 601, thus allowing staple holder 308 to pivot with respect to shaft 317 about axle 601. As would be appreciated by those skilled in the art, rotation of thumbwheel 74 resulting in a proximal (i.e., rightward with respect to the view shown in FIGS. 6A and 6B) motion of drive rod 603 will cause a corresponding counterclockwise rotation of staple holder 308 and staple 305 to, for example, the position of holder 308 shown in solid in FIG. 6A. Conversely, rotation of thumbwheel 606 which results in distal (i.e., leftward with respect to the view shown in FIGS. 6A and 6B) motion of drive rod 603 will cause a corresponding clockwise rotation of staple holder 308 and staple 305 about axle 601 to, for example, position 302" shown in phantom in FIG. 6A.

When a surgeon is inserting instrument 300 (FIG. 3A) into a patient, thumbwheel 606 is manipulated to pivot staple holder 308, and consequently needle 302 to the closed position 302", so that needle 302 will not interfere with passing working end 301 through a canula to the surgical site. After insertion, a surgeon may manipulate thumbwheel 606 to pivot the staple holder 308 and staple 305 as required. For example, a surgeon may pivot staple holder 308 to a fully opened position (shown in solid in FIG. 6A) to skewer a graft, and then return the staple holder to a home position 302' or the closed position 302" to prevent the graft from falling off while the graft is positioned adjacent to an artery. Subsequently, the thumbwheel 606 may again be manipulated to position the staple holder 308 at an open position so that the needle 302 can skewer the artery to be joined with the graft. In some cases, a surgeon may wish to fix the position of needle 302 with respect to working end 301. Various known mechanisms (not shown) such as thumbwheel detents or adjustable drag devices, as well as drive rod clamps and the like may be provided for this purpose.

While piercing or manipulating grafts, arteries, or other tissues, various forces are applied to the needle 302. Therefore, the staple holder 308 must be sufficiently strong to withstand these forces, and capable of maintaining the needle 302 in a fixed position as selected by the surgeon. In a preferred embodiment of instrument 300, loading forces applied to the needle 302 are transmitted through drive rods 303 and 305 and thumbwheel 606, so that a surgeon receives tactile feedback from instrument 300 as the surgery is progressing.

Figure 3B:
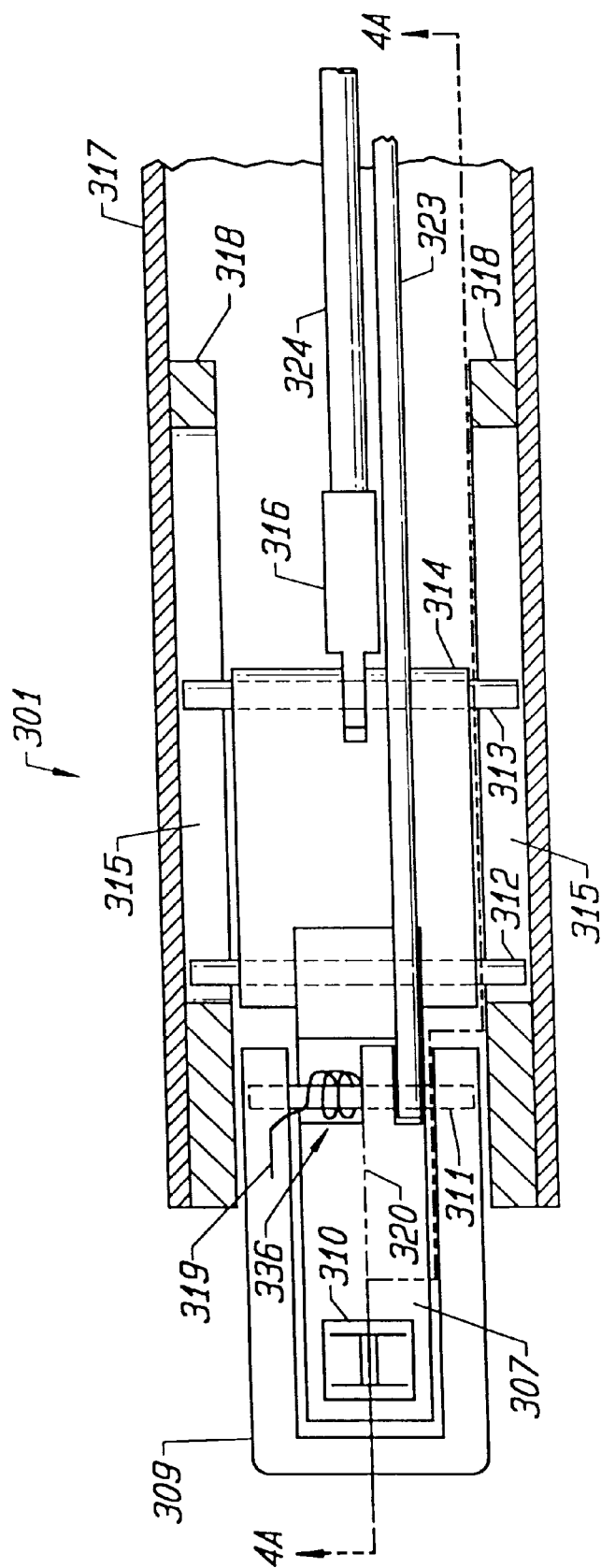
FIG. 3B is a plan view, in section, of the distal end of the instrument with the staple closing members shown.

The mechanisms for removing needle 302 (FIG. 4A) and for bending flange 304 and pin 303 to form a completed staple out of unformed staple 305 will now be described with reference to FIGS. 3B–5H. Referring specifically first to FIGS. 3B–3D, needle removal member 307 is in general provided for gripping needle 302 and removing it from staple 305. Staple forming member 309 is in general provided for bending pin 303 and flange 304 to form a completed staple, and for maintaining the tissue and graft, pierced by needle 302, captured on pin 303 while the staple is being closed. Needle removal member 307 fits within staple forming member 309, and members 307 and 309 are mounted on a common shaft through pivot access 311. A torsion spring 336 is wound around pivot access 311 and connected between needle removal member 307 and staple forming member 309 so as to bias staple forming member 309 into the page as shown in FIG. 3B relative to needle removal member 307. Needle removal member 307 is in turn biased by drive rod 323, mounted to needle removal member 307 at pivot access 311, and by drive rod 324 which is connected to needle removal member 307 at pivot access 312 via carriage 314 and connector piece 316, as explained hereinafter. The needle removal member 307 may include a small protrusion 307a that lies in contact with a lower surface of the staple forming member 309. Thus, as the needle removal member rotates clockwise (with respect to FIGS. 3C and 4A) as explained hereinafter, the protrusion 307a causes the staple forming member to undergo a similar clockwise rotation.

Needle removal member 307 is manipulated by controls in handle end 335, as described hereinafter, to be brought down over the tip of needle 302, and to subsequently carry needle 302 away from unformed staple 305. Referring specifically to FIGS. 3B–3C and 3F–3G, needle removal member 307 includes a gripper 310 having a gripping member 340 and a needle stabilizer 341. Gripping member 340 is comprised of two locking members 343 and 344 protruding diagonally upward toward each other to define an aperture 342 through which needle 302 is received. As explained hereinafter, needle removal member 307 is positioned over needle 302 such that the counterclockwise motion of needle removal member 307 (as shown in FIGS. 4C and 4D) causes needle 302 to be inserted into gripper 310. Upon subsequent clockwise rotation of the needle removal member 307 (as shown in FIGS. 4D and 4E), needle 302 is held by gripper 310 due to its contact with the sharp edges of resilient locking members 343 and 344, and the force moments such contact induces in locking members 343 and 344. Specifically, the greater the extraction force upon needle 302, the greater the force moments induced in locking members 343 and 344. Sufficiently strong force moments will cause the sharp edges of locking members 343 and 344 to plastically deform needle 302 with their points of contact against members 343 and 344. Such plastic deformation of needle 302 by locking members 343 and 344, in addition to the frictional contact between needle 302 and members 343 and 344, ensures that needle 302 will be securely held by gripper 310 upon insertion of needle 302 therein. Upon being inserted into gripper 310, needle 302 will also penetrate needle stabilizer 341. Needle stabilizer 341 prevents needle 302 from rotating substantially about its contacts with locking members 343 and 344.

Gripping member 340 is typically made of a resilient, hard material which is preferably stainless steel. In order to plastically deform needle 302, it is also preferable that the material of which gripping member 340 is made be harder than the material of needle 302. Gripping member 340 may be press fit into a hole formed in needle removal member 307 and securely fixed therein. Needle stabilizer 341 is preferably made of a soft, elastomeric material, such as silicone. The stabilizer 341 is shaped to fit into the hole in needle removal member 307 above gripping member 340.

Referring now to FIGS. 3B and 3D, staple forming member 309 includes gate head 306 which is used to bend pin 303 and flange 304 down over the base of the staple after needle removal member 307 has removed needle 302 from the staple 305. Staple forming member 309 further includes vertical stops 338 which serve to stop the counterclockwise rotation (with respect to the view of FIG. 3D) of the member 309 by contacting the horizontal top surface of staple holder 308. Gate head 306 and vertical stops 338 also serve to keep the tissue and graft, pierced by needle 302, captured on pin 303 while the staple is being completed.

Figure 4A:
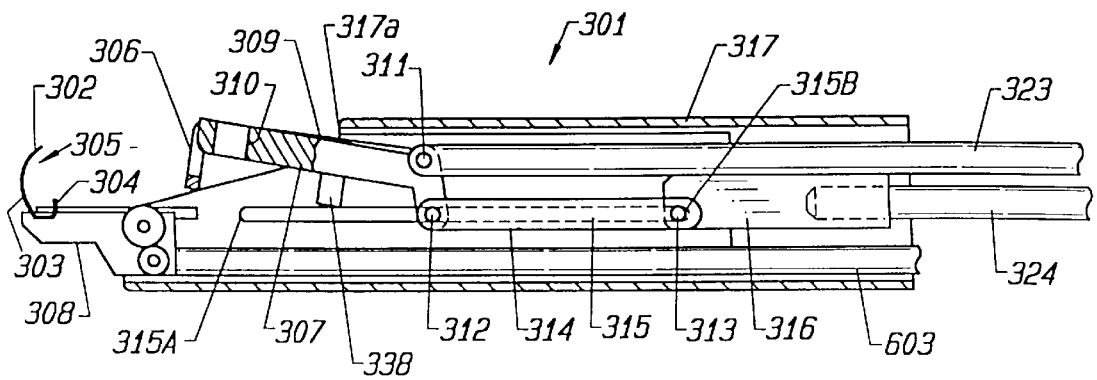
FIGS. 4A–4I show how a closed staple is formed by the assemblies at the distal end of the instrument, with FIG. 4A being a sectional view through line 4A—4A on FIG. 3B.
Figure 4B:
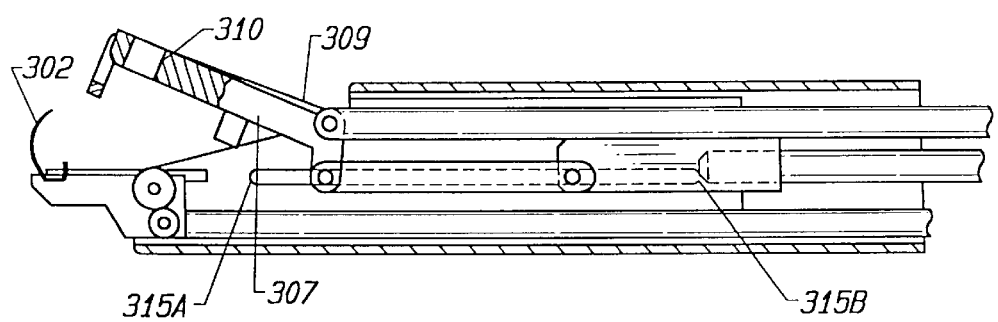
Figure 4C:
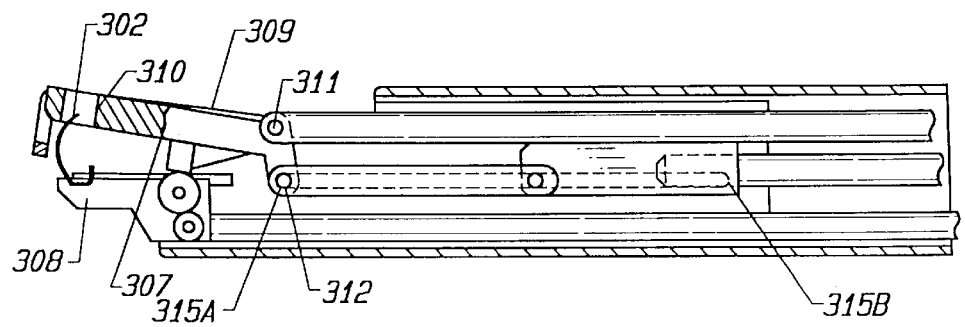
Figure 4D:
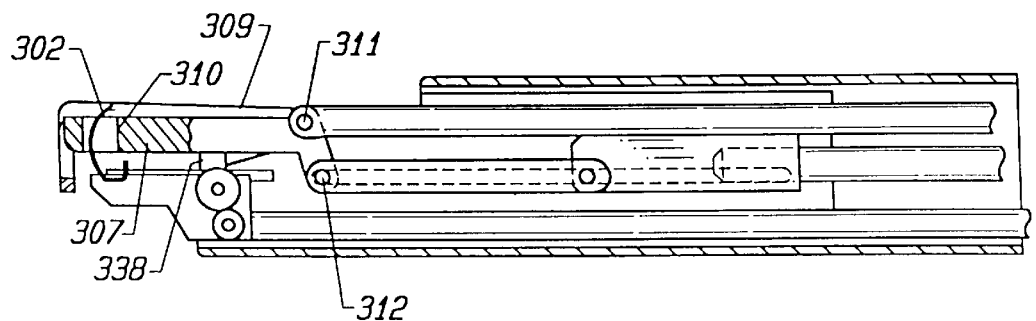
Figure 4E:
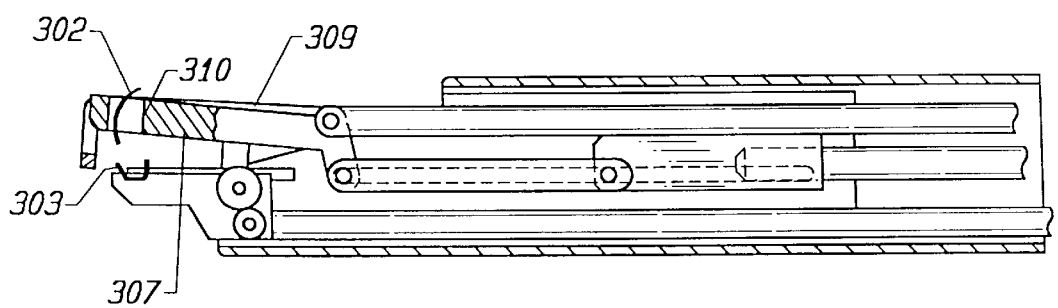

Referring now to FIGS. 3B, 3E and 4A, needle removal member 307 is affixed to a carriage 314 by a pin 337 running through pivot access 312. Distal end 301 of instrument 300 includes a frame 318 fitting within tubular housing 317. A pair of slots 315 are formed in frame 318, and carriage 314 rides within slots 315 via shafts running through pivot axes 312 and 313. Carriage 314 riding in slots 315 assures substantially lateral movement of pivot axis 312 in a horizontal plane. Connector piece 316 is connected at one end to carriage 314, and at the other end to drive rod 324.

The movement and manipulation of needle removal member 307 and staple forming member 309 will now be described with reference to FIGS. 4A–5H. FIGS. 4A–4I illustrate the movements of needle removal member 307 and staple forming member 309, whereas FIGS. 5A–5H illustrate the components in the handle end 335 for affecting the movement of members 307 and 309. Referring to FIG. 4A, the needle removal member 307 and staple forming member 309 are shown in section through line 4A—4A on FIG. 3B. Staple 305 is held by a base of the staple on needle holder 308. After the tissues to be fastened are skewered onto needle 302 and positioned on pin 303, needle holder 308 is returned to the home position shown in FIG. 4A in preparation for closing of the staple 305.

Referring now to FIG. 5A, needle removal member 307 and staple forming member 309 are manipulated by a slide 321 and a release button 322 manually operated by a surgeon. Drive rod 323 is fixedly mounted to slide 321, and slide 321 is also indirectly coupled to drive rod 324 via a slider 328 and a guide 329. Guide 329 is preferably a cylindrical chamber housing slider 328 and a spring 330. Slider 328 is also a cylindrical member, designed to slide laterally within the cylindrical chamber of guide 329. A distal end (i.e., to the left in FIG. 5A) of slider 328 is open to receive spring 330. Spring 330 is preferably a helical spring compressed between a distal end of guide 329 and a proximal end of slider 328. As such, spring 330 biases slider 328 against a proximal end of guide 329.

The drive rod 323 is fixedly mounted to slider 328 via a pin 323*a* such that there is one-to-one lateral translation between slide 321, drive rod 323 and slider 328. Drive rod 324 is fixedly mounted to guide 329 such that there is one-to-one lateral translation between guide 329 and drive rod 324. Rods 323 and 324 slide through holes provided in a wall 331. Similarly, guide 329 is fixedly mounted at its proximal end to a shaft 324*a*, which shaft 324*a* slides through a hole in a wall 332. The engagement of rod 323, rod 324, and shaft 324*a* through holes in walls 331 and 332 ensure purely lateral movement of rod 323, rod 324, and guide 329.

Handle end 335 further includes a cantilever 325 pivotally mounted to slide 329 at a pivot point 325*a*. Cantilever 325 includes ends 326 and 327, and a torsion spring (not shown) biasing cantilever 325 to rotate in a counterclockwise direction (with respect to the view shown in FIG. 5A). An upward force on end 327 can be applied by pressing release button 322. Release button 322 is preferably attached to handle end 335 by a leaf spring 350 biasing release button 322 to project outward and away from handle end 335. In an unbiased position (i.e., absent actuation of release button 322), end 326 fits through a hole formed in guide 329 into a space 352 initially defined between the proximal ends of slider 328 and guide 329.

While tissues are being skewered on needle 302, the needle removal member 307 and the staple forming member 309 are preferably in a retracted position shown in FIG. 4A, and therefore do not obstruct the surgeon's view of needle 302 or of the needle holder 308. At this point, the components in the handle end 335 are in their position shown in FIG. 5A. The first step in closing unformed staple 305 is to depress release button 322 to rotate cantilever 325 and remove end 326 from space 352. In a preferred embodiment, an upper surface of members 307 and 309 are in contact with an edge 317*a* of housing 317 such that the members 307 and 309 are initially constrained against rotation in the clockwise direction with respect to the views shown in FIG. 4A. As the members 307 and 309, and consequently, rods 323 and 324, are initially constrained against relative movement, removal of end 326 of cantilever 325 from space 352 will not cause any significant movement of slider 328 with respect to guide 329; that is, in the preferred embodiment, removal of end 326 from space 352 while members 307 and 309 are in their retracted positions will not result in slider 328 moving proximally in guide 329 to close space 352.

The next step in forming completed staple 305 is to move slide 321 distally as shown in FIG. 5B. Distal movement of slide 321 will result in distal movement of drive rod 323, and consequently, distal movement of needle removal member 307 and staple forming member 309. Once free of edge 317*a*, members 307 and 309 are free to rotate in a clockwise direction. As spring 330 is biasing slider 328 proximally, or rearward, with respect to guide 329 (and consequently, drive rod 323 rearward with respect to drive rod 324), freeing of the members 307 and 309 from edge 317*a* causes the members 307 and 309 to rotate clockwise at pivot axes 311 and 312 as a result of the slider 328 moving rearward in guide 329 to close space 352. Thus, distal movement of slide 321 will cause drive rod 323 and 324 to both move distally. However, as the members 307 and 309 clear edge 317*a*, the spring 330 causes drive rod 324 to move distally to a greater extent than drive rod 323, thereby rotating members 307 and 309 to the positions shown in FIG. 4B.

With slider 328 located against the rear or proximal wall of guide 329 (FIG. 5C), continued distal movement of slide 321 will move guide rods 323 and 324 distally together, until the pivot point 312 reaches an edge 315*a* of slot 315 (FIG. 4C). The movement of rods 323 and 324 together occurs as a result of slide 321 directly moving rod 323 distally; and slide 321 moving slider 328 distally via drive rod 323, slider 328 moving guide 329 distally as a result of spring 330, and guide 329 moving drive rod 324 distally.

Once pivot access 312 reaches the edge 315a of slot 315, further distal actuation of slide 321 and drive rod 323 (FIG. 5D) will cause rod 323 to move distally while rod 324 remains stationary. Such relative motion between rods 323 and 324 causes needle removal member 307 and staple forming member 309 to rotate counterclockwise (FIGS. 4C and 4D). The distal motion of drive rod 323 while drive rod 324 remains stationary also causes slider 328 to move distally with respect to guide 329. As opposed to pivot point 312 contacting end 315a of slot 315, distal movement of drive rod 324 may be stopped as a result of a distal edge of guide 329 abutting against wall 331. This too will affect counterclockwise rotation of members 307 and 309 as shown in FIGS. 4C and 4D.

With the needle removal member 307 in the position shown in FIG. 4D, needle 302 is received within and grasped by needle gripper 310 as described above. Additionally, as a result of the torsion spring within cantilever 325, once slider 328 has moved distally with respect to guide 329 to once again create a space 352, cantilever 325 rotates counterclockwise to once again position end 326 in space 352 as shown in FIG. 5C.

In the next step of forming a completed staple, slide 321 is released, thereby causing slider 328 to move slightly in the proximal direction relative to guide 329 due to the biasing force of spring 330. The slider 328 moves proximally until the proximal edge of slider 328 lies in contact with end 326 of cantilever 325 as shown in FIG. 5E. The proximal motion of slider 328 relative to guide 329 (and consequently proximal motion of guide rod 323 relative to guide rod 324) causes a slight clockwise rotation of needle removal member 307 and staple forming member 309 as shown in FIG. 4E. As needle 302 is securely gripped by needle gripper 310, this slight clockwise rotation causes needle 302 to be pulled off of staple 305.

Figure 4F:
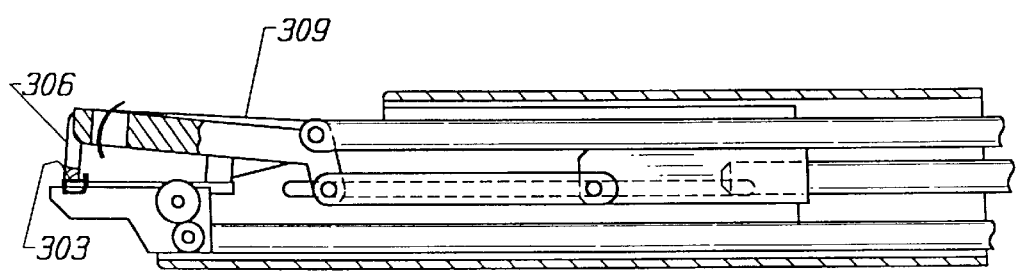

As shown in FIG. 5F, slide 321 is next slid proximally. Such translation moves guide rod 323 proximally, and, as slider 328 is abutting against cantilever end 326, guide 329 and drive rod 324 also move proximally with slide 321 and drive rod 323. As shown in FIG. 4F, such movement of drive rods 323 and 324 together moves staple forming member 309 proximally such that gate head 306 contacts and bends pin 303 down over the tissues (not shown) and the base of the staple.

Figure 4G:
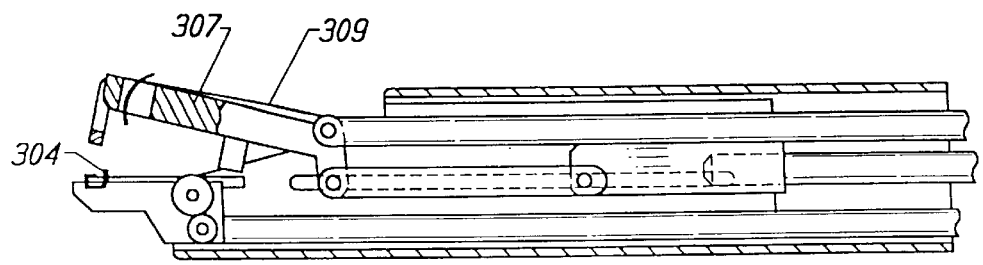

Referring now to FIGS. 5F and 5G, release button 322 includes an incline 334. During the proximal movement of guide 329 by slide 321, end 327 of cantilever 325 will ride up incline 334 (release button 322 is at this point still being actuated by the surgeon). As a result, end 326 of cantilever 325 will be drawn out of space 352. Upon removal of end 326 from space 352, spring 330 will bias slider 328 rearward until it contacts the proximal end of guide 329. Such relative movement between slider 328 and guide 329 will cause a corresponding relative movement between drive rods 323 and 324, thus resulting in a clockwise rotation of needle removal member 307 and staple forming member 309 as shown in FIG. 4G. Such rotation of members 307 and 309 allows gate 306 of staple forming member 309 to clear flange 304 as member 309 moves proximally.

Figure 4H:
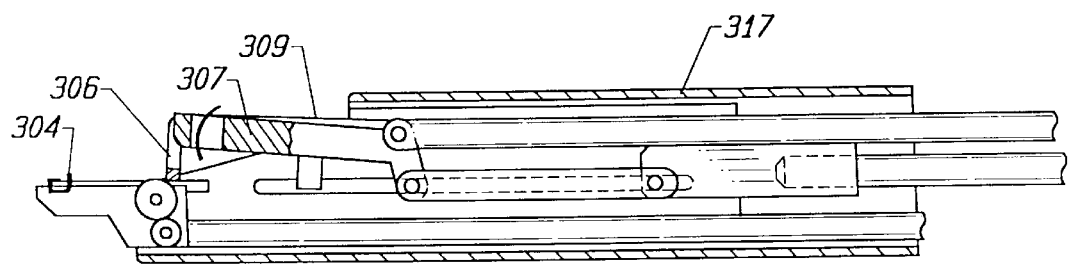

With continued proximal movement of slide 321, needle removal member 307 and staple forming member 309 will eventually contact the upper edge 317a of housing 317, which contact will rotate members 307 and 309 in a counterclockwise direction as shown in FIG. 4H. Such counterclockwise rotation will move drive rod 324 proximally relative to drive rod 323. As shown in FIG. 5H, proximal movement of drive rod 324 relative to drive rod 323 induces a corresponding proximal movement of guide 329 relative to slider 328, thus once again creating the space 352 between the proximal ends of the slider 328 and guide 329. Release button 322 has at this point been released by the surgeon, thus allowing end 326 of cantilever 325 to pivot into the space 352 as a result of the spring-biased force within cantilever 325. Walls 332 and 333 may limit the proximal movement of guide 329, rods 323 and 324, and members 307 and 309.

Figure 4I:
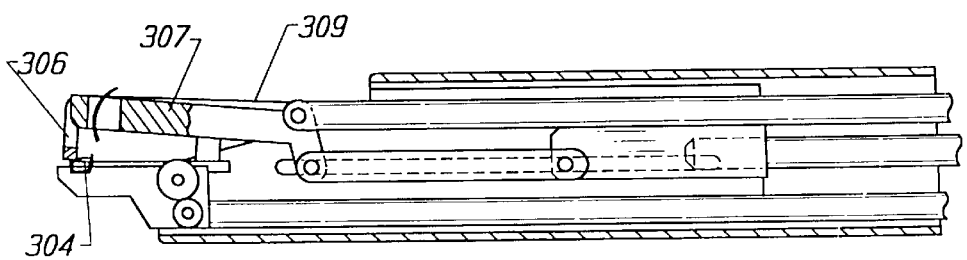

The final step in forming completed staple 305 is shown in FIG. 4I. Slide 321 is moved distally from its position shown in FIG. 5H, without depressing release button 322. As a result, drive rod 323 and 324 simply translate distally without any relative motion between them. Distal movement of drive rods 323 and 324 in turn results in a distal movement of needle removal member 307 and staple forming member 309 such that gate head 306 of staple forming member 309 win contact and bend flange 304 down over pin 303.

It win be readily understandable to those with skill in the art that the drive mechanism of handle 335 as described above is only one possible means for manipulating rods 323 and 324 and members 307 and 309 to achieve the closing of the staple. Other known manual or automatic actuation systems may be used to bring about the above-described motions of needle removal member 307 and staple forming member 309 to thereby form a closed staple 305. In embodiments of the present invention including a needle 302 integrally formed as part of unformed staple 305, it is necessary to first cut needle 302 from staple 305 prior to bending of the pin 303 and flange 304 by staple forming member 309. As previously stated, a mechanism as recited in U.S. patent application Ser. No. 08/781,578 may be used to sever the needle. In such an embodiment, the instrument 300 may be modified to omit those portions of the instrument whose function it is to remove the needle 302.

Figure 7D:
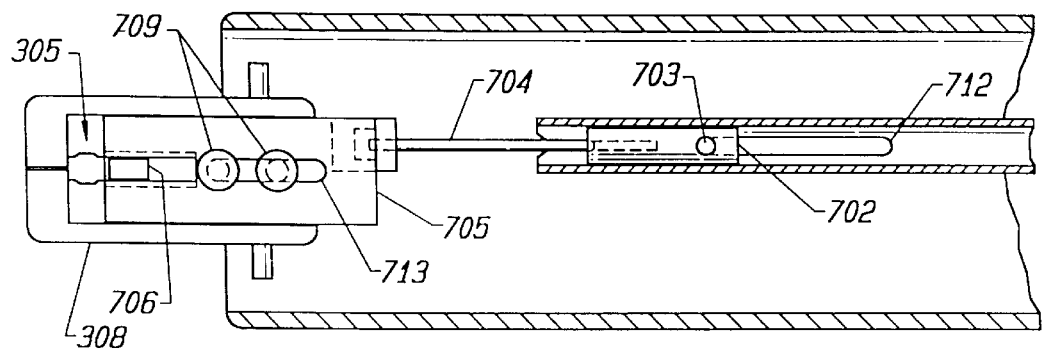
FIGS. 7D–7F show plan views of the distal end of the staple instrument at three stages of the staple latching process.
Figure 7E:
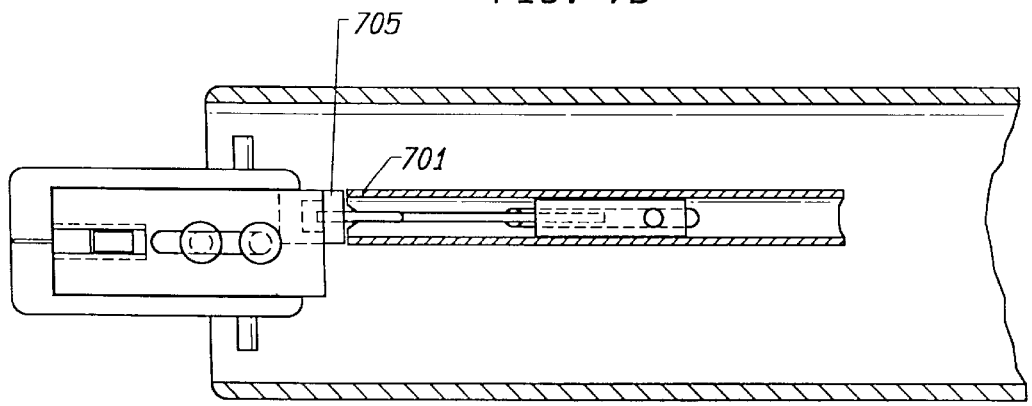
Figure 7F:
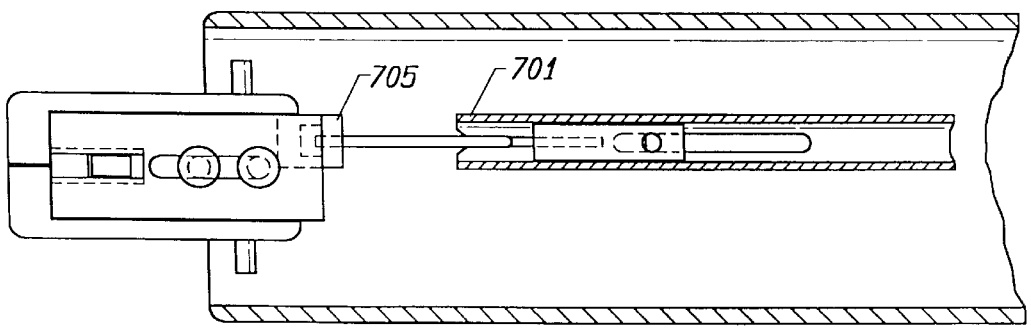

FIGS. 7A and 7B show, respectively, side views of distal end 301 and handle 335 with respect to a mechanism for latching an unformed staple in the staple holder 308. FIG. 7C shows an isometric view of staple holder 308, while FIGS. 7D–7F are plan views of distal end 301 at three states of the latching process. Referring to FIG. 7A, a staple 305 is depicted as being held by back stop 706 and latch plate 705. In FIG. 7A, staple 305 is latched by latch plate 705, which is shown in its most distal position, and covering the wings 8 (FIG. 1C) of staple 305. As shown in FIG. 7C, back stop 706 is designed to hold the base of staple 305 with the pin of staple 305 fitting partially into recess 710. FIG. 7C also shows mounting holes 708 for latch plate 705. The mounting holes 708 receive rivets 709 (FIGS. 7A and 7D), which rivets are mounted through a slot 713 formed in latch plate 705 and then into holes 708. This mounting arrangement allows the latch plate 705 to be slidably mounted on staple holder 308.

FIG. 7D illustrates latch plate 705 in its most rightward or proximal position. In this position, a staple 305 may be loaded onto back stop 706 in preparation for application of a staple 305 to a surgical site, and in this position, a staple 305 which has been closed around the tissues to be fastened may be released from the instrument 300. Latch plate 705 is slid between its extreme rightward and leftward positions by the following means depicted in FIG. 7A. A wire 704 is attached to latch plate 705 at pivot axis 707. The other end of wire 704 is attached rigidly to a cylindrical plug 702 which is designed to slide within drive rod 701. Rod 701 may be hollow throughout its length, or only at distal end 301. Rigidly attached to plug 702 is cylindrical stop 703. Cylindrical stop 703 is designed to project through top and bottom slots 712 in rod 701 (one such slot is shown in FIGS. 7D–7F). As shown in FIG. 7B, rod 701 continues into handle 335 where it is connected to a slide 711 for one-to-one motion with slide 711. In FIG. 7D, unlatching has been accomplished by the surgeon moving slide button 711 proximally to its rightmost position. This moves rod 701 to the right, which pulls plug 702 to the right when stop 703 contacts the leftmost edge of slots 712. Plug 702 pulls latch plate 705 rightward by wire 704.

FIG. 7E illustrates latching being accomplished by the surgeon moving slide 711 distally to its leftmost position. This moves rod 701 to the left until the leftmost edge of rod 701 contacts the rightmost edge of latch plate 705. Further leftward movement of rod 701 then directly pushes latch plate 705 leftward until it covers wings 308 of staple 305.

Once the staple 305 is latched to back stop 706, the surgeon then moves slide button 711 partially rightward again as shown in FIG. 7F. Since rod 701 is only moved partially rightward, stop 703 does not contact the leftmost edge of slots 712. Rather, stop 703 is sufficiently centered within slots 712 such that staple holder 308 can be tilted, as described above, without stop 703 contacting either the leftmost or rightmost edge of slots 712. It will be readily understandable to those of skill in the art that the drive mechanism of handle 335 is only one possible means for moving latch plate 705. For example, in one alternative embodiment, the rod 701 could be fixedly attached directly to latch plate 705 by suitable affixing mechanisms, so that there is a one-to-one movement of latch plate 705 with slide 711.

Up to this point, the assemblies in the working end have been described as being actuated and controlled by manually operated thumbwheels and slides in the handle end of the instrument. However, in alternative embodiments of the invention, it is understood that removal of the needle from the unformed staple, formation of the completed staple, and its release from the applier may be automated by driving the drive rods and distal mechanisms of the instrument through their ranges of motion by motors, actuators, pneumatic or hydraulic systems, or some other force transmission mechanism instead of or in addition to the manual actuation of the drive rods and distal mechanisms as described above. In such an embodiment, the motors, actuators and/or other force transmission mechanisms may be activated by known, manually activated switches or buttons in the handle end of the instrument. As would be appreciated by those skilled in the art, actuation of the drive rods to affect the motions of the various assemblies in the working end as described above may be accomplished by affixing the proximal ends of the drive rods to the motors, actuators and/or force transmission mechanisms to bring about the desired controlled movement of the drive rods and working end assemblies and therefore automate these functions. Additionally, force limiters may be provided to limit the force with which the motors and/or actuators drive the drive rods and tube. The force limiters may be mechanical, such as of the type in U.S. Ser. No. 08/781,577, previously incorporated by reference, or the force limiters may be electrical, such as closed loop feedback signals which monitor the amount of force exerted on the drive rods and/or distal end assemblies.

In a further embodiment of the present invention, it is contemplated that the manually operated mechanisms in the handle end may be omitted, and the assemblies in the working end of the instrument may be actuated and controlled by a surgical robot, to which shaft 317, and the assemblies and mechanisms contained therein, are attached. In such an embodiment, motors, actuators, pneumatic/hydraulic systems and/or other force transmission mechanisms may be provided as described above for driving the drive rods and assemblies in the working end of the instrument for forming and releasing a completed staple. The motors, actuators and/or other force transmission mechanisms may in turn be controlled remotely by a computer and/or a surgeon.

This invention also supplies a method of attaching soft tissues together in the chest, abdominal cavity, and retroperitoneal space, and for attaching a graft to an artery in these same areas. This invention is particularly useful for minimally invasive surgical procedures, especially for performing an anastomosis between a vascular graft and an artery. The method is applicable to arteries from 1–2 millimeters in diameter (such as coronary arteries), and to larger arteries (such as the aorta, iliac arteries, and femoral arteries).

The method uses the instrument of the invention containing at least one open staple to apply the staple and form a surgical fastener, as described above. A small incision is made in the patient's abdominal cavity, chest, or retroperitoneal space, depending on the clinical situation, and the distal or working end of the elongated shaft of the instrument is inserted through this opening. In carrying out a vascular anastomosis, the surgeon preferably first inserts the needle through the exterior wall of a vascular graft. The needle is then inserted through the interior lumen of the artery, and through the arterial wall at the appropriate location. If the artery is heavily calcified, the surgeon may make a hole in the artery, using a punch or other device, before inserting a blunt tipped needle through the arterial wall. Once the needle is in place—through both the graft and the arterial wall—the surgeon employs the instrument to move those tissues onto the pin, remove the needle, and form the staple to permanently secure the graft and the arterial wall together on the pin and between the base and the flange. This method results in the anastomotic edges of the graft and artery being substantially everted, and the staple lying in an extraluminal position. This procedure, therefore, isolates the intra-luminal area from coming in contact with the staple. As described above, the pin, base and flange are designed so the surfaces in contact with the artery on one side and the graft on the other are sufficient to spread the forces of contact enough to ensure viability of the artery, while providing a hemostatic seal between graft and artery. Those surfaces are also sufficiently large to prevent migration of the staple through the graft or the artery after application.

The method may involve repeating these steps to apply a series of additional staples. These steps are repeated with additional staples being applied around the anastomotic lumen, until the artery and graft have been joined together in a substantially hemostatic relationship. The number of staples will vary with the size of the artery and the circumference of the anastomosis. Typically, between about 8 and about 25 staples may be used for a typical end to end anastomosis between the aorta and a vascular graft. The method may also be used in conjunction with other surgical fasteners, such as vascular clips, or with conventional suturing, to provide a hemostatic anastomosis. This method is useful in end-to-end, side-to-end and side-to-side procedures. In the construction of a vascular anastomosis, these staples are applied at positions and locations identical to those used for conventional sutures, and suturing techniques.

Hence, the staples may be applied to within about 0.5 millimeters to about 5 millimeters from the cut edge of the arterial wall, and within no less than 3 threads of the cut end of a prosthetic, woven graft, as the absolute minimum.

This invention also supplies a method of attaching soft tissues together, located in the chest, the abdominal cavity, and in the retroperitoneal space, and for attaching a graft to an artery in these same areas. This invention is particularly useful for minimally invasive surgical procedures, especially for performing an anastomosis between a vascular graft and an artery. The method is applicable to arteries ranging size from 1—2 millimeters in diameter (such as coronary arteries), up to larger arteries, such as the aorta, iliac arteries, and femoral arteries.

The method of vascular grafting using this present invention may be illustrated in the context of an endoscopic aortobifemoral bypass procedure. The patient is positioned on the operating room table midway between a right lateral decubitus position and a supine position, resulting in availability of the left flank and both groins to be sterilely prepared for operation. The table is slightly flexed to open the iliac crest-costophrenic angle. A standard sterile preparation of the patient is performed. Standard draping technique is accomplished. Standard vertical groin incisions are made to mobilize the common femoral, superficial femoral, and profunda femoral arteries in each groin. By finger dissection, a tunnel toward the abdominal cavity is made from each incision by palpation along the course of the common femoral artery just superior to the common femoral artery and just below the inguinal ligament. The tunnel is extended as far as a finger can palpate.

Along the mid axillary line as drawn to the iliac crest midway between the iliac crest and the ribs a small incision is made in the skin and subcutaneous tissue. Utilizing finger dissection, dissection is carried down through the fat to the posterior muscles. A balloon dissector is then placed through this small incision at this location and a cavity created. When the balloon dissector has created a cavity in the potential space between the retroperitoneal fat and the psoas muscle then the cavity is further expanded by placing a sealed port and insufflating $CO_2$. Once insufflating has been accomplished, the space is examined and a correct relationship between the lateral and anterior abdominal walls is established so then in the centermost portion of the roof of the cavity a port is made to insert a lifting device. The dissection continues without further $CO_2$ insufflation.

Several small incisions are made in the abdominal wall to carefully position abdominal wall retractors which are attached to the lifting device. With the space now developed and the aorta exposed from the renal vein to the bifurcation and the left iliac artery exposed to the left hypogastric artery, further dissection is accomplished superiorly around the aorta and each of the lumbar vessels and also just above the right common iliac artery. Care is again taken to ensure not entering the peritoneal cavity. The aorta is completely dissected free just below the renal arteries which are identified visually, and each of the lumbar vessels is controlled with temporary arterial staples. The quality of the pulse in the aorta is confirmed by comparison with preoperative angiograms to ensure that the correct area for anastomosis of the bypass graft has been obtained and that the aorta is soft and pliable and will accept surgical staples. Dissection is then completed to both groins and the tunnels that were started in each groin is noted to be complete by passing a tunneler from the groin along the previously palpated space of the iliac artery to the retroperitoneal cavity (created by the primary dissection of the aorta).

A correctly sized graft is then selected and fashioned to ensure that the bifurcation length is appropriate, and the proximal end is trimmed for either an end-to-end or end-to-side anastomosis. The graft is then introduced through a port into the dissected space and each of the limbs are appropriately positioned in the groins where they will ultimately be attached. An appropriate aortic clamp is selected to clamp the aorta just below the renal arteries, and another clamp is selected for clamping the aorta at the level of the inferior mesenteric artery. The aorta is cross-clamped. Ischemia time begins at this point and the operation is directed to be done as expeditiously as possible.

If an end-to-end anastomosis is planned, then the aorta is divided and excess aorta is removed to permit exposure of the end of the infra renal aorta. The graft which has been previously positioned is then held by graspers, and the system of the invention is utilized to attach the graft to the aorta. Each staple is placed in turn at appropriate spacing to ensure correct sealing of the graft to the aorta. After all staples have been placed and secured, a clamp that may grasp either limb of the graft is applied to the limbs of the graft, and the aorta clamp is temporarily opened to distend the graft with normal pulsatile arterial flow. Upon noting a secure anastomosis, the proximal aortic clamp is removed, however if any leak points are noted, another staple is applied or sewn into place positioned to close the bleeding point.

When hemostasis is secure, the left limb of the graft is passed though the tunnel by grasping it with a grasper from the groin incision and the graft is delivered into the groin wound. A standard end of graft to side of common femoral or profunda femoris artery is performed. A similar process is utilized for the right groin. Each graft limb in turn is opened to flow upon satisfactory completion of the anastomosis. The staples are used to sew closed the stump of the distal aorta. Areas are inspected to ensure adequate hemostasis, and when this is ensured, wounds are irrigated with antibiotic solution. The retroperitoneal cavity is then allowed to collapse upon the newly placed graft. No closure of this cavity is required as the ports and laprolift are removed. Laparoscopic wounds are then closed in standard fashion ensuring absorbable sutures close the small fascial defects and the skin wounds are steri-stripped. The open groin wounds are then closed in standard fashion utilizing three layers for closure of each wound and the skin edges are approximated with staples.

It is to be understood that the embodiments shown as described above are only illustrative of the principles of the invention, and various modifications can be made by those skilled in the art without departing from the scope and spirit of the invention, such as joining together any two tissues present in the abdomen, chest, or retroperitoneum. The skilled artisan will also appreciate that the present invention can be practiced by other than the described embodiments, which are provided for purposes of illustration and not of limitation, and that the present invention is only limited by the claims that follow.

We claim:

1. A surgical fastener comprising:

a base having at least one substantially planar surface, a flange bendably joined to a first edge of the base and having at least one substantially planar surface adapted to cooperate with the planar surface of the base, a pin bendably joined to the base at a second edge of said base opposing the first edge, and a needle substantially longer than the pin for skewering tissues, or tissue and graft, the needle being removably joined to the pin to receive the tissues, or tissue and graft, from the needle, the pin and flange capable of bending over the base to fix the tissues, or tissue and graft, together.

2. A surgical fastener defined in claim 1 wherein the base is configured to be releasably engaged with an associated applying instrument.

3. A surgical fastener for securing portions of tissues, or tissue and graft, together comprising:
   base means having at least one substantially planar surface,
   flange means bendably joined to a first edge of the base means and having at least one substantially planar surface for cooperating with the planar surface of the base means,
   pin means bendably joined to the base means at a second edge of said base opposing the first edge, and
   needle means removably joined to the pin means for piercing tissues, or tissue and graft, wherein the base means and the flange means each have cooperating surfaces to contact and secure on the pin means portions of tissues, or tissue and graft, to be joined together.

4. A surgical fastener defined in claim 3 wherein the base means includes means for releasably engaging an associated applying instrument.

5. An instrument for applying a surgical staple comprising:
   an elongated shaft having a distal end portion,
   a staple holder at the distal end portion adapted to engage a staple and a needle removably joined to the staple, wherein the needle is substantially longer than any member of the staple, and the staple includes a base including at least one substantially planar surface, a flange bendably joined to a first edge of the base and having at least one substantially planar surface adapted to cooperate with the planar surface of the base, and a pin bendably joined to an edge of the base opposing said first edge,
   a staple forming member at the distal end portion adapted to bend the pin over a substantial portion of the base and to bend the flange over a substantial portion of the pin, so that the staple is substantially closed, and
   a handle having a control for actuating the staple forming member.

6. An instrument defined in claim 5 wherein the elongated shaft has a length and width adapted for use in minimally invasive surgery.

7. An instrument as defined in claim 5 wherein the base is configured to be releasably engaged by the staple holder, and the handle has a control for releasing the staple after it is closed.

8. An instrument as defined in claim 5 wherein the staple holder is also adapted to articulate the needle relative to the elongated shaft, and the handle has a control for actuating an articulating mechanism.

9. An instrument as defined in claim 5 wherein the instrument further comprises a needle removal member at the distal end portion adapted to remove the needle from the staple.

10. An instrument as defined in claim 5 wherein:
    the base and the flange each have cooperating surfaces to contact and secure on the pin portions of tissues to be joined or portions of a graft to an artery.

11. An instrument as defined in claim 10 wherein the elongated shaft has a maximum diameter less than about 20 millimeters.

12. An instrument for applying a surgical staple comprising:
    an elongated shaft having a distal end portion,
    staple holder means at the distal end portion for holding a staple and a needle removably attached to the staple for piercing tissues, or tissue and graft, wherein the needle is substantially longer than any member of the staple, and the staple comprises base means having at least one substantially planar surface for securing tissues or grafts, flange means bendably joined to one edge of the base means and having at least one substantially planar surface for cooperating with the planar surface of the base means to secure tissues or grafts, and pin means bendably joined to the base means at an opposing edge for holding tissues or grafts, wherein the base means and the flange means each have cooperating surfaces to contact and secure on the pin means portions of tissues to be joined together or portions of a graft to an artery,
    staple forming means associated with the staple holder means for bending the pin means over a portion of the base means, and for folding the flange means over a substantial portion of the pin means so that the staple is substantially closed, and
    a handle having control means for actuating the staple forming means.

13. An instrument defined in claim 12 wherein the elongated shaft has a length and width adapted for use in minimally invasive surgery.

14. An instrument as defined in claim 12 wherein the base means includes means for releasably engaging the staple holder means, and the handle has control means for releasing the staple after it is closed.

15. An instrument as defined in claim 12 wherein the staple holder means includes means to articulate the needle relative to the elongated shaft, and the handle has control means for actuating such articulation means.

16. An instrument as defined in claim 12 wherein the instrument further comprises needle removal means at the distal end portion for removing the needle from the pin means.

17. An instrument as defined in claim 12 wherein the elongated shaft has a maximum diameter less than about 20 millimeters.

18. A method for attaching soft tissues located in the abdominal cavity, chest and retroperitoneal space and for attaching a graft to an artery in these areas comprising:
    providing an instrument for applying a surgical staple having an elongated shaft with a distal end portion and having a staple forming member at the distal end portion adapted to bend portions of a staple,
    providing a staple holder at the distal end of the instrument with at least one staple, and a needle attached to each at least one staple, the at least one staple comprising a base having at least one substantially planar surface, a flange bendably joined to one edge of the base and having at least one substantially planar surface adapted to cooperate with the planar surface of the base, and a pin bendably joined to the base at an opposing edge, wherein the base and the flange each have cooperating surfaces to contact and secure on the pin portions of tissues to be joined together or portions of a graft to an artery,
    incising a patient's tissue to create at least one opening into the patient's abdominal cavity, chest or retroperitoneal space, inserting the distal end of the instrument through the opening, so that the distal end is disposed in the patient, passing the needle through a portion of one tissue, graft or artery and through a portion of a second tissue, artery or graft, and actuating the staple forming member to bend the pin over a substantial portion of the base and to bend the flange over a substantial portion of the pin, so that the staple is substantially closed.

19. The method defined in claim 18 wherein the passing and actuating steps are repeated to apply additional staples.

20. The method defined in claim 18 wherein the incising step creates a small incision and wherein the inserting, passing and actuating steps are performed by minimally invasive surgical procedures.

21. The method defined in claim 18 wherein the shaft of the needle is passed through a portion of a first graft or artery and through a second artery or graft to form a portion of an artery to graft anastomosis.

22. A surgical staple system for fastening together tissues, or tissue and graft, comprising:

a first member with a needle removably joined to the first member, said needle being substantially longer than the first member and adapted to pass through the tissues, or tissue and graft;

a second member adjacent to said first member; and a third member adjacent to said second member, said second and third members capable of moving from a first orientation, where portions of said members are spaced apart sufficiently to receive the tissues, or tissue and graft therebetween, to a second orientation where said members lie in contact with the tissues, or tissue and graft.

23. A surgical staple as recited in claim 22, wherein said first member is capable of being bent with respect to said second member and said third member has a recess adapted to receive at least a portion of said first member.

24. A surgical staple system for fastening tissues, or tissue and graft, together, comprising:

a base having a substantially planar surface and adapted to be releasably gripped by a staple applying instrument;

a flange having a substantially planar surface attached to a first edge of said base, said flange capable of moving from a first position, where said substantially planar surfaces of said flange and base are spaced apart sufficiently to receive the tissues, or tissue and graft, therebetween, to a second position, where said substantially planar surfaces of said base and flange lie in contact with the tissues, or tissue and graft; and a pin attached to a second edge of said base different from said first edge, said pin adapted to releasably join with a needle substantially longer than said pin, said pin capable of moving from a first position, where said pin and said substantially planar surface of said base are spaced apart sufficiently to receive the tissues, or tissue and graft, therebetween, to a second position, where said pin and said substantially planar surface of said base lie in contact with the tissues, or tissue and graft.

25. A surgical staple system as recited in claim 24 further comprising a needle releasably joined to said pin.

26. A surgical staple system for fastening tissues, or tissue and graft, together, comprising:

a staple including at least a first section adjacent to a second section, said first and second sections capable of moving from a first orientation, where said first and second sections are spaced apart sufficiently to receive the tissues, or tissue and graft, therebetween, to a second orientation, where said first and second sections lie in contact with the tissues, or tissue and graft; and a single needle capable of aligning and skewering the tissues, or tissue and graft, said needle being attached to one of said first or second sections of said staple.

27. A surgical fastener system, comprising:

a staple including at least first and second joined sections, said first and second sections capable of moving from a first orientation, where said first and second sections are spaced apart sufficiently to receive the tissues, or tissue and graft, therebetween, to a second orientation, where said first and second sections lie in contact with the tissues, or tissue and graft;

a single needle affixed adjacent to an end of one section of said at least first and second joined sections; and an instrument capable of manipulating said needle in a minimally invasive procedure such that said needle skewers a first tissue or graft, aligns said first tissue or graft to a desired position with respect to a second tissue or graft, and skewers said second tissue or graft, and said instrument capable of folding said at least first and second joined sections with respect to each other to secure said first tissue or graft to said second tissue or graft between said at least first and second joined sections of the staple.

28. A surgical staple system for fastening tissues, or tissue and graft, together, comprising:

a staple including a first section joined to a second section;

a single needle affixed to said staple for skewering the tissues, or tissue and graft, and for locating the tissues, or tissue and graft, in a desired position with respect to the staple, said needle being substantially longer than either said first section or said second section of said staple; and an instrument having a proximal and distal end, including:
  means in said distal end for holding said staple,
  means in said distal end for articulating said staple,
  means in said distal end for bending said first section with respect to said second section in a minimally invasive procedure,
  controls located remotely from said distal end for actuating said staple holding means, said staple articulating means, and said bending means, and
  connecting means for connecting said controls in the proximal end with the staple holding means, said staple articulating means, and said bending means in said distal end.

29. A surgical staple system as recited in claim 28, wherein said needle is articulated by said means for articulating said staple.

30. A surgical staple system as recited in claim 29, further comprising means for removing said needle from said staple.

31. A surgical staple system as recited in claim 30, wherein means for bending said first section with respect to said second section and said means for removing said needle from said staple retract proximally from said distal end to provide a clear line of sight for a surgeon to said needle while said means for articulating said staple articulates said needle.

32. An instrument including distal and proximal ends for fastening tissues, or tissue and graft, together with a staple in a minimally invasive surgical procedure, the staple including a base, a flange attached to a first edge of said base, and a pin attached to an edge of said base other than the first edge, the pin having a needle removably mounted thereon for skewering the tissues, or tissue and graft, comprising:

a staple holder in the distal end for holding the staple and needle;

means in the distal end for articulating said staple holder, to manipulate the needle such that the needle skewers the tissues, or tissue and graft, on the needle in a desired position with respect to each other, and positions the tissues, or tissue and graft, on the pin;

means in the distal end for removing the needle from the staple;

a staple forming member in the distal end, including:
  means for bending the pin down over the base, and
  means for bending the flange down over the pin and base;

controls located remotely from said distal end for actuating said means for articulating said staple holder, said means for removing the needle, and said staple forming member; and connecting means spanning between the distal and proximal ends of the instrument for connecting said controls to said means for articulating said staple holder, said means for removing the needle, and said staple forming member.

33. An instrument including distal and proximal ends for fastening tissues, or tissue and graft, together as recited in claim 32, wherein said means for removing the needle from the staple and said staple forming member retract proximally from said distal end to provide a clear line of sight for a surgeon to said needle while said means for articulating said staple holder manipulates said needle.

34. An instrument including distal and proximal ends for fastening tissues, or tissue and graft, together as recited in claim 32, wherein said controls comprise hand-actuated controls.

35. An instrument including distal and proximal ends for fastening tissues, or tissue and graft, together as recited in claim 32, wherein said controls comprise automated robotic controls.

36. An instrument including distal and proximal ends for fastening tissues, or tissue and graft, together as recited in claim 32, wherein said controls and said connecting means together comprise an automated robotic system for actuating said means for articulating said staple holder, said means for removing the needle, and said staple forming member.

37. An instrument including distal and proximal ends for fastening tissues, or tissue and graft, together as recited in claim 32, further comprising a motor, controlled by said controls, for actuating said connecting means.

38. An instrument including distal and proximal ends for fastening tissues, or tissue and graft, together as recited in claim 32, further comprising pneumatic means, controlled by said controls, for actuating said connecting means.

39. An instrument including distal and proximal ends for fastening tissues, or tissue and graft, together as recited in claim 32, further comprising hydraulic means, controlled by said controls, for actuating said connecting means.

40. A surgical fastener as recited in claim 39 wherein said first member defines a hole providing passage for at least a portion of said first member therethough.

41. A surgical staple system as recited in claim 26 wherein said needle is removably attached to one of said first or section sections of said staple.

42. A surgical staple system as recited in claim 26 wherein said needle is fixedly attached to one of said first or second section of said staple.

43. A surgical staple system as recited in claim 42 wherein one of said first or second sections defines a hole providing passage for at least a portion of said needle therethrough.

44. A surgical staple system as recited in claim 26 wherein said needle is integral with one of said first or second sections of said staple.

45. A surgical staple system as recited in claim 44 wherein one of said first or second sections defines a hole providing passage for at least a portion of said needle therethrough.

46. A surgical staple as recited in claim 22, further comprising a piercing implement removably joined to said first member.

47. A surgical fastener as recited in claim 22 wherein said first member includes a piercing end.

* * * * *

UNITED STATES PATENT AND TRADEMARK OFFICE
CERTIFICATE OF CORRECTION

| | |
|---|---|
| PATENT NO. | : 6,149,658 |
| APPLICATION NO. | : 08/781579 |
| DATED | : November 21, 2000 |
| INVENTOR(S) | : Gardiner et al. |

It is certified that error appears in the above-identified patent and that said Letters Patent is hereby corrected as shown below:

Column 26, line 18, that portion of the claim reading "claim 39" should read --claim 22--.

Signed and Sealed this

Ninth Day of September, 2008

JON W. DUDAS
*Director of the United States Patent and Trademark Office*